(12) United States Patent
Chiuh et al.

(10) Patent No.: US 11,246,898 B2
(45) Date of Patent: Feb. 15, 2022

(54) ANTIVIRAL ARTHROSPIRA MAXIMA EXTRACT

(71) Applicant: FAR EAST BIO-TEC CO., LTD., Taipei (TW)

(72) Inventors: Chuang-Chun Chiuh, Taipei (TW); Yi-Hsiang Chen, Taipei (TW); Gi-Kung Chang, New Taipei (TW); Jing-Yun Chen, Taichung (TW); Ya-Chun Liao, Taipei (TW); Xin-Wen Huang, Taipei (TW); Shin-Ru Shih, Taoyuan (TW); Wei Chen, Miaoli (TW)

(73) Assignee: FAR EAST BIO-TEC CO., LTD., Taipei (TW)

(*) Notice: Subject to any disclaimer, the term of this patent is extended or adjusted under 35 U.S.C. 154(b) by 0 days.

(21) Appl. No.: 16/803,439

(22) Filed: Feb. 27, 2020

(65) Prior Publication Data

US 2020/0197458 A1 Jun. 25, 2020

Related U.S. Application Data

(63) Continuation of application No. PCT/US2018/048918, filed on Aug. 30, 2018.

(60) Provisional application No. 62/552,045, filed on Aug. 30, 2017.

(51) Int. Cl.
| | |
|---|---|
| *A61K 36/02* | (2006.01) |
| *A23L 33/135* | (2016.01) |
| *A61P 31/12* | (2006.01) |
| *A61P 11/00* | (2006.01) |
| *A61K 9/00* | (2006.01) |
| *A61K 31/715* | (2006.01) |
| *A61L 15/58* | (2006.01) |

(52) U.S. Cl.
CPC ............ *A61K 36/02* (2013.01); *A23L 33/135* (2016.08); *A61K 9/0014* (2013.01); *A61K 31/715* (2013.01); *A61L 15/58* (2013.01); *A61P 11/00* (2018.01); *A61P 31/12* (2018.01); *A61K 2236/331* (2013.01)

(58) Field of Classification Search
None
See application file for complete search history.

(56) References Cited

U.S. PATENT DOCUMENTS

| 9,657,263 B2 * | 5/2017 | Chiuh | .................. C12N 1/04 |
| 2017/0080035 A1 * | 3/2017 | Chiuh | .................. A61K 35/748 |
| 2017/0136075 A1 * | 5/2017 | Choung | ............... A23L 33/105 |
| 2020/0276251 A1 * | 9/2020 | Chiuh | .................. A61K 31/675 |

FOREIGN PATENT DOCUMENTS

| CN | 1278691 C | 10/2006 |
| WO | WO-02/04000 A1 | 1/2002 |
| WO | WO-2015/096856 A1 | 7/2015 |

OTHER PUBLICATIONS

Chaiklahan R. et al. Polysaccharide Extraction from *Spirulina* sp. and Its Antioxidant Capacity. Int J of Biological Macromolecules 58:73-78, Jul. 2013. (Year: 2013).*

Nie et al., "Fractionation and characterization of polysaccharides from cyanobacterium *Spirulina* (Arthrospira) *maxima* in nitrogen-limited batch culture," J. Cent. South Univ. Technol. vol. 9, No. 2, 2002, p. 81-86, 6 pages.

Wei Chang, "Isolation and Analysis of Intracellular Active Substances from *Spirulina maxima*," 2005, Master thesis, Department of Applied Chemistry, Nanjing Tech University, 36 pages.

Wang et al., "A simple strategy for the separation and purification of water-soluble polysaccharides from the fresh *Spirulina platensis*," Separation Science and Technology, 2017, vol. 52, No. 3, p. 456-466, 11 pages.

Majdoub et al., "Anticoagulant activity of a sulfated polysaccharide form the geen alga *Arthrospira platensis*," Biochemica and Biophysica Acta 1790, 2009, p. 1377-1381, 5 pages.

Tefera et al., Importance of Arthrospira [*Spirulina*] in Substainable Development, International Journal of Current Trends in Pharmacobiology and Medical Sciences, vol. 1, No. 2, 2016, p. 60-68, 9 pages.

International Search Report of PCT/US2018/48918, dated Jan. 15, 2019, 1 page.

Search Report of TW Application No. 107130394, completed on Dec. 16, 2019, 2 pages.

Armida Hernandez-Corona et al, "Antiviral activity of Spirulina maxima against herpes simplex virus type 2", Antiviral Research 56 (2002) pp. 279-285.

Toshimitsu Hayashi et al., "Calcium Spirulan, an Inhibitor of Enveloped Virus Replication, from a Blue-Green Alga *Spirulina platensis*", J. Nat. Prod. 1996, pp. 59, 83-87.

Korean Office Action, patent application No. 10-2020-7005778, dated Jun. 17, 2021, 10 pages.

* cited by examiner

*Primary Examiner* — Ralph J Gitomer
(74) *Attorney, Agent, or Firm* — Muncy, Geissler, Olds & Lowe, P.C.

(57) ABSTRACT

The present disclosure provides various cyanobacterial extracts exhibiting antiviral activity to a wide spectrum of viruses, such as enterovirus (EV), respiratory syncytial virus (RSV), Human Herpesvirus (HHV), Ebola virus, porcine epidemic diarrhea virus (PEDV), and porcine reproductive and respiratory syndrome virus (PRRSV). The cyanobacterial extract is prepared from biomass of *A. maxima* (or *Spirulina maxima*). Also disclosed herein are process for preparing the cyanobacterial extract and uses of the cyanobacterial extract.

7 Claims, 6 Drawing Sheets

ANTIVIRAL ARTHROSPIRA MAXIMA EXTRACT

CROSS-REFERENCE TO RELATED APPLICATIONS

This application is a continuation application of International Patent Application No. PCT/US2018/048918, filed Aug. 30, 2018, which relates to and claims the benefit of U.S. Provisional Application No. 62/552,045, filed Aug. 30, 2017, the content of these applications is incorporated herein by reference in their entirety.

BACKGROUND OF THE INVENTION

1. Field of the Invention

The present invention relates to a novel cyanobacterial extract, process for preparing the same and the use thereof. In particular, the cyanobacterial extract exhibits antiviral activity to a wide spectrum of viruses, such as enterovirus (EV), respiratory syncytial virus (RSV), Human Herpesvirus (HHV), Ebola virus, porcine epidemic diarrhea virus (PEDV), and porcine reproductive and respiratory syndrome virus (PRRSV).

2. Description of the Related Art

Cyanobacteria are microscopic bacteria found in land and fresh, brackish, or marine water. Cyanobacteria carry out oxy-genic photosynthesis. Because they are photosynthetic, aquatic cyanobacteria are commonly referred to as blue-green algae. Currently, there are more than 2,000 described species under the cyanobacteria phylum. Cyanobacteria have been identified as a rich source of biologically active compounds with antiviral, antibacterial, antifungal and anticancer activities. Isolated compounds from cyanobacteria belong to groups of polyketides, amides, alkaloids, fatty acids, indoles, and lipopeptides. Efforts are being made to identify active extract fractions or compounds with desired therapeutic effects.

Spirulina refers to the dietary supplement made from the dried biomass of *Arthrospira platensis* and *A. maxima*. *A. maxima* (or *Spirulina maxima*) are found in tropical or subtropical areas with salty and alkali water bodies. For example, it is common in Lake Chad, Africa, and Lake Texcoco, Mexico. These two species were once classified in the genus *Spirulina*. Although according to the current taxonomy, the name *Spirulina* for these two strains is inappropriate, and agreement exists that the genus *Arthrospira* includes *A. platensis* and *A. maxima*, the outdated taxonomy is still used today, and the dietary supplements made therefrom are most often referred to by their popular name, spirulina. Spirulina has been used as a food source since ancient Aztec times. When used as the dietary supplement, spirulina is often provided as a dried powder, which is rich in proteins and polysaccharides and also contain numerous essential nutrients, such as B vitamins and dietary minerals (e.g., iron and manganese).

Enteroviruses (EVs) are a genus of positive-sense single-stranded RNA viruses that are named by their transmission-route through the intestine. EVs are first classified into polioviruses, Coxsackie A viruses (CA), Coxsackie B viruses (CB), and echoviruses, based on their pathogenesis. Later identified EVs are named as Enteroviruses followed by consecutive numbers, such as, EV68, EV69, EV70, EV71. The first outbreak of Human Enterovirus type 71 (EV71) in Taiwan took place in 1998, which caused a totally of 405 severe cases and 80 deaths. In China, an epidemic upsurge of EV71 in 2010, resulted in more than 1.7 million cases, with 27,000 patients having severe neurological complications and 905 fatalities. EV71 infection is known to cause hand, foot, and mouth disease (HFMD), and during 2011 to 2014, there were millions HFMD cases reported in China. Every year, hundreds of children in China are dead because of the EV71 infections. Accordingly, there exists an urgent need in the related art to provide an effective vaccine, as well as anti-EV71 drugs. As of 2014, there are three completed phase III clinical trials in China, whereas in Taiwan and Singapore, they each has one completed phase I trial. The vaccine protection efficacy is more than 90% in EV71-induced HFMD, and 80% in EV71-associated diseases. However, EV71 is currently divided into four genotypes (A, B, C and D genotypes) and is further divided into 12 sub-genotypes. Therefore, the cross-species protective efficacy of the EV71 vaccine derived from a specific strain with single genotype against other prevalent virus is uncertain. In view of the foregoing, a broad-spectrum anti-EV71 or anti-enterovirus drug for EV71 prevention and treatment is important.

Respiratory syncytial virus, or RSV, is a common respiratory virus that usually causes mild, cold-like symptoms. In the United States, 60% of infants are infected during their first RSV season, and nearly all children will have been infected with the virus by 2-3 years of age. Of those infected with RSV, 2-3% will develop bronchiolitis, necessitating hospitalization. Although there is much active investigation into the development of new vaccines for RSV, at present no such vaccine exists. On the other hand, the treatment of RSV has been limited to supportive measures. Since the development of a commercial RSV vaccine has remained elusive, a broad-spectrum anti-RSV drug for RSV prevention and treatment is important.

Human Herpesviruses (HHVs) are DNA viruses that infect human. including herpes simplex viruses (HSV) 1 and 2 (also known as HHV1 and HHV2), varicella-zoster virus (VZV or HHV-3), Epstein-Barr virus (EBV or HHV-4), human cytomegalovirus (HCMV or HHV-5), human herpesvirus 6A and 6B (HHV-6A and HHV-6B), human herpesvirus 7 (HHV-7), and Kaposi's sarcoma-associated herpesvirus (KSHV or HHV-8). This group of viruses is characterized in the latent and recurring infection. Some antiviral drugs are known to ameliorate the symptoms associated with HHV infection; however, there is no drug that can eliminate the HSV from the site of latency (e.g., neuron, T cell, B cell, or monocyte).

Ebola virus belongs to Filoviridae classified within the Mononegavirales. Member viruses of the order Mononegavirales are enveloped viruses composed of linear, non-segmented, negative sense, single-stranded RNA genome. Because of the high mortality rate, potential for person-to-person transmission, and lack of effective vaccine or antiviral therapy, Ebola virus is classified as biosafety level-4 (BSL-4) pathogens. Although ring vaccination of Ebola vaccine appeared to be somewhat effective, but the extent of efficacy was uncertain. Also, there are further Ebola virus strains circulating around the Africa, and gene mutations on the viral RNA genome also make it more challenging to develop an effective vaccine. Therefore, it is important to develop agents with anti-Ebola activity so as to treat and/or prevent Ebola infection to prepare for unexpected outbreak emergencies.

In sum, there exists an urgent need in the related art for a broad-spectrum antiviral drug against various viruses, especially enterovirus, respiratory syncytial virus, Ebola virus, porcine epidemic diarrhea virus and porcine reproductive and respiratory syndrome virus so as to prevent and/or cure the viral infection. On the other hand, although various biological or physiological properties of the Spirulina extract have been reported or described generally, there is no prior evidence suggesting the anti-viral activity of the Spirulina extract against these viruses.

SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In a first aspect, the present disclosure is directed to a cyanobacterial extract, in particular, the extract from *A. maxima* (hereinafter, the *Arthrospira maxima* extract or AM extract for short). The present AM extract is characterized in having an increased amount of total sugars (in particular, neutral and/or positively charged polysaccharides), which is positively correlated with their antiviral activity. As discussed below, this unique composition of the present AM extract results in a desirable antiviral activity against a wide range of viruses. Moreover, experimental data provided below further establish that this AM extract still retains a satisfactory antiviral activity upon the treatment with the digestive enzyme. Since oral ingestion is the most common route of administration for the AM extract, the antiviral activity after the digestive enzyme treatment suggests that there is a higher chance that the AM extract, upon enteral administration (e.g., oral administration), can survive the first pass metabolism and elicit the antiviral effect in vivo.

According to some embodiments of the present disclosure, the AM extract comprises at least 25% (wt %) of the total sugar. For example, the present AM extract may comprise 25-75% (wt %) of the total sugar.

In some embodiments, the AM extract is derived from a high-molecular-weight fraction obtainable using a filter membrane having a molecular weight cut-off (MWCO) of 100 KD.

In certain embodiments, the AM extract comprises at least 60% (wt %) of neutral and/or positively charged polysaccharides based on the total sugars in the extract. Optionally, the present AM extracts may comprise 60-100% (wt %) of neutral and/or positively charged polysaccharides based on the total sugars in the extract.

According to various embodiments of the present disclosure, the AM extract comprises rhamnose as the major glycosyl component. For instance, the rhamnose may account for at least 30 mol % of all glycosyl components in the AM extract.

In some embodiments, the most abundant glycosyl linkage of the polysaccharides in the AM extract is 3-rhap.

In certain embodiments, the AM comprises a protein content of less than 20% (wt %).

In another aspect, the present disclosure is directed to processes for preparing the AM extract according to the above-mentioned aspect-embodiment(s) of the present disclosure. By using the unique extraction processes presented herein, one may produce AM extracts with increased sugar content and/or reduced protein content, as compared with extracts obtained by conventional extraction processes.

According to certain embodiments of the present disclosure, the process for preparing the AM extract comprises the steps of, extracting *Arthrospira maxima* biomass in hot water of 80-120° C. to obtain a crude mixture; removing solid residues from the crude extract to obtain a hot-water extract; and optionally, drying the hot-water extract to obtain hot-water extract powder. The hot-water extract is rich in sugar content and comprises less protein content, as compared with extracts obtained by conventional extraction methods, such as cold-water extraction.

In further optional embodiments, the process may comprise the steps of, subjecting the hot-water extract or a solution comprising the hot-water extract powder to filtration using a filter membrane having a molecular weight cut-off value of 100 KD to obtain a high-molecular-weight fraction; and optionally drying the high-molecular-weight fraction to obtain high-molecular-weight extract powder. The experimental data presented herein demonstrate that the high-molecular-weight extract exhibits even better antiviral activity than the hot-water extract does, whereas the low-molecular weight extract is not effective in inhibiting the viral infection.

Still optionally, the present extraction may further comprise the steps of, subjecting the high-molecular-weight fraction or a solution comprising the high-molecular-weight extract powder to an anion-exchange chromatography using an anion-exchange column; collecting the effluent flowing through the anion exchange column, wherein the effluent comprises AM extract rich in positively-charged and/or neutral polysaccharides; eluting the anion exchange column with a salt solution and collecting the elution, wherein the elution comprises AM extract rich in negatively-charged polysaccharides; and optionally, drying the effluent or the elution respectively to obtain extract powder rich in positively-charged or neutral polysaccharides and extract powder rich in negatively-charged polysaccharides. The AM extract rich in positively-charged and/or neutral polysaccharides is even more effective in terms of the antiviral activity than the high-molecular-weight extract and the AM extract rich in negatively-charged polysaccharides is.

In some embodiments, the anion exchange column is a diethyl aminoethyl (DEAE)-based column, quaternary aminoethyl (QAE)-based column or a trimethylamino ethane (TMAE)-based column, or other positively-charged columns.

In another aspect, the present disclosure is directed to a method for treating a viral infection or a disorder caused by the viral infection, in a subject in need thereof. The experimental data provided herewith evidence that the AM extract according to the above-mentioned aspect/embodiment(s) of the present disclosure is effective against a wide range of viruses, such as, Enterovirus virus (EV), respiratory syncytial virus (RSV), Ebola virus, porcine epidemic diarrhea virus (PEDV), and porcine reproductive and respiratory syndrome virus (PRRSV).

According to some embodiments of the present disclosure, the method comprises the step of administering to the subject an effective amount of the present AM extract.

In various embodiments, the subject is a mammal, including human.

In yet another aspect, the present invention is directed to a method for inhibiting viral replication of a specified virus in a host cell.

According to embodiments of the present disclosure, the method comprises the step of exposing the host cell to an effective amount of the AM extract according to the above-mentioned aspect/embodiment(s) of the present disclosure.

In various embodiments, the method may be carried in vitro or in vivo. The host cell may be a mammalian cell.

In still another aspect, the present disclosure is directed to a nutraceutical or pharmaceutical composition for treating a viral infection or a disorder caused by the viral infection.

According to some embodiments, the nutraceutical or pharmaceutical composition comprises an effective amount of AM extract and, optionally, a nutraceutically- or pharmaceutically-acceptable excipient.

The present invention is also directed to a biocompatible material, which comprises a biocompatible matrix and AM extract distributed within the biocompatible matrix or across the surface of the biocompatible matrix. For example, the biocompatible material may be a gel or spray solution, which comprises a biocompatible vehicle and the AM extract distributed within the biocompatible vehicle. In another example, the biocompatible may be a patch which comprises an absorbent solid support, which may be impregnated with the AM extract gel or solution. In still another example, one surface of the patch of the biocompatible material may be coated with an adhesive layer comprising the AM distributed within the adhesive layer.

Subject matters that are also included in other aspects of the present disclosure include the use of AM extract in the manufacture of a medicament for use in the treatment of a viral infection or a disorder caused by the viral infection, as well as AM extract for use in the treatment of a viral infection or a disorder caused by the viral infection.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1:
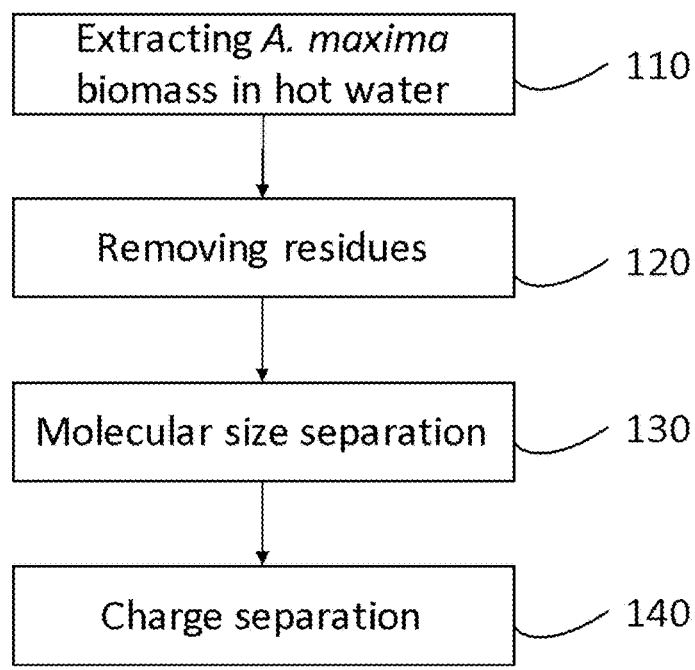
FIG. 1. Is a flow chart illustrating the process for preparing various AM extracts according to various embodiments of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the examples. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The terms "treatment" and "treating" as used herein may refer to a preventative (e.g., prophylactic), curative or palliative measure. In particular, the term "treating" as used herein refers to the application or administration of the present AM extract or a pharmaceutical composition comprising the same to a subject, who has a medical condition, a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition. In the present disclosure, the disease, disorder and/or condition intends to cover a virus infection caused by the specified viruses and a disease, disorder and/or condition associated or derived from the virus infection. In preferred embodiments, the present AM extract can be used to inhibit the viral replication both in vitro and in vivo. Accordingly, the present treatment method provides means for substantially eradicating the infectious pathogens in the host organism such that the pathogen is not-detectable in the host organism.

The terms "subject" and "patient" are used interchangeably herein and are intended to mean an animal including the human species that is treatable by the present AM extract, pharmaceutical composition, and/or method of the present invention. The term "subject" or "patient" intended to refer to both the male and female gender unless one gender is specifically indicated.

The terms "application" and "administration" are used interchangeably herein to mean the application of the present AM extract or a pharmaceutical composition of the present invention to a subject in need of a treatment thereof.

The term "effective amount" as used herein refers to the quantity of the present AM extract that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of mammal or animal being treated, the duration of the treatment, the nature of concurrent therapy (if any), and the specific formulations employed and the structure of the active component or its derivatives. Effective amount may be expressed, for example, as the total mass of AM extract (e.g., in grams, milligrams or micrograms) or a ratio of mass of the AM extract to body mass, e.g., as milligrams per kilogram (mg/kg).

The phrase "nutraceutically- or pharmaceutically-acceptable excipient" as used herein means a material, composition or vehicle, such as a liquid or solid filler, diluent, carrier, solvent or encapsulating material, involved in carrying or transporting the subject agents from one organ, or portion of the body, to another organ, or portion of the body. Each excipient must be "acceptable" in the sense of being compatible with the other ingredients of the formulation. The nutraceutical or pharmaceutical formulation contains the AM extract of the invention in combination with one or more nutraceutically- or pharmaceutically-acceptable ingredients. The excipient can be in the form of a solid, semi-solid or liquid diluent, cream or a capsule. These nutraceutical or pharmaceutical preparations are a further object of the invention. Usually, the amount of the AM extract is between 0.1-95% by weight of the preparation, preferably between 0.2-20% by weight in preparations for parenteral use and preferably between 1 and 50% by weight in preparations for oral administration. For the clinical use of the methods of the present invention, the nutraceutical or pharmaceutical composition of the invention is formulated into formulations suitable for the intended route of administration, such as oral administration.

As used here the term "biomass" is meant biomass derived from a culture containing *A. maxima*. This term includes the living and dead organisms, as well as a ready-made, dried, frozen or otherwise previously worked biomass.

The present disclosure is based, at least in part, on the discovery that the present *A. maxima* extract (AM extract) is capable of inhibiting the viral infection caused by a wide range of viruses, such as, EV, RSV, HHV, Ebola virus, PEDV, and PRRSV. In view of the foregoing, the present disclosure proposes methods for treating viral infection caused by the specified viruses. Some embodiments of the present disclosure are directed to methods for treating disorders caused by such viral infection. Also provided herein is the use of said AM extract for use in the treatment of said viral infection, as well as for use in the manufacture of a medicament for said treatment purpose. The medicament (i.e., a pharmaceutical composition) is, of course, a subject matter covered by the scope of the present application.

According to some embodiments of the present disclosure, the AM extract is rich in sugar contents. For example, the AM extract comprises at least 25% (wt %) of the total sugar, such as 25, 30, 35, 40, 45, 50, 55, 60, 65, 70, 75, and 80% (wt %) of the total sugar based on the total weight of the AM extract. The experimental data provided below demonstrate that such sugar-rich AM extract is effective in inhibit virus replication of a vast array of viruses, whereas conventional AM extract with less sugar content does not exhibit such high-level of antiviral activity.

The present AM extract is also unique in that it comprises a reduced amount of proteins, as compared with conventional AM extract. According to various embodiments of the present disclosure, the protein level of the AM extract is less than 20% (wt %), such as 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, and 20% (wt %) based on the total weight of the AM extract.

According to some further embodiments, the AM extract is a high-molecular-weight AM extract that is derived from a high-molecular-weight fraction obtainable from a molecular size separation means. In some optional embodiments, the high-molecular-weight fraction is obtained by filtering the sugar-rich AM extract with a filter membrane having a molecular weight cut-off (MWCO) of 100 KD. Generally, MWCO, in the context of the filter membrane, refers to the lowest molecular weight molecule (in Daltons) in which a defined percentage (e.g., 80, 85, 90 or 95%) of the molecule is retained by the filter membrane during the filtration (or dialysis) procedure. Therefore, the high-molecular-weight fraction comprises an increased amount of constituents having a molecular weight of more than 100 KD, as compared with the low-molecular weight fraction does. Experimental data presented below indicate that the present high-molecular-weight AM extract elicits a more satisfactory antiviral efficacy, compared with the sugar-rich hot-water extract or the low-molecular-weight AM extract.

In further embodiments, the high-molecular-weight AM extract is further refined using a charge separation means. For example, the high-molecular-weight AM extract is subjected to an anion exchange chromatography so that the constituents in the extract are further separated based on the charge of the molecules. The anion exchange chromatography yields a fraction that is rich in positively-charged and/or neutral polysaccharides and another fraction rich in negatively-charged polysaccharides. Experimental data included hereinbelow establish that the AM extract with predominantly positively-charged and/or neutral polysaccharides is more effective in inhibiting virus replication of specified viruses, compared with the high-molecular-weight AM extract and the AM extract with mostly negatively-charged polysaccharides.

According to various embodiments of the present disclosure, the high-molecular-weight AM extract comprises at least 60% (wt %) of neutral and/or positively charged polysaccharides based on the total sugars in the extract. For example, the neutral and/or positively charged polysaccharides may account for 60-100 (wt %) of the total sugar in the extract. For example, the AM extract may comprise 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 (wt %) of the neutral and/or positively charged polysaccharides based on the total sugar content.

According to certain embodiments of the present disclosure, rhamnose is the major glycosyl component among the glycosyl components constituting the polysaccharides in the AM extract. In some optional embodiments, the AM extract has at least 30 mol % of rhamnose based on the total glycosyl components in the AM extract. For example, the mole percent of the rhamnose may be 30, 32, 34, 36, 38, 40, 42, 44, 45, 46, 48, 50, 52, 54, 55, 56, 58, 60, 62, 64, 65, 66, 68, or 70 mol %.

Also, the most abundant glycosyl linkage present in the polysaccharides is 3-rhap, according to some embodiments of the present disclosure. For example, in one working example, more than half of the rhamnose residues has the 3-rhap linkage.

As could be appreciated, various AM extracts are described herein. Although some claimed AM extracts may exhibit a better antiviral activity than other claimed AM extracts do, these sugar-rich AM extracts yield an higher antiviral activity with higher sugar contents. Further, experimental data provided below establish that the present AM extract still retains a satisfactory antiviral activity upon the treatment with the digestive enzyme, suggesting that they may elicit the desired antiviral effect in vivo. Moreover, there are many measures and techniques known in the art to formulate the present AM extract so as to enhance the bioavailability and/or efficacy of the orally-ingested AM extract.

In addition to the AM extracts described above, the present disclosure also provides a process for preparing such AM extracts. The process is characterized in a hot-water extraction step, which results in an increase in the total sugar content of the AM extract and enhance the antiviral activity. The present process also comprises additional steps to refine the AM extracts, thereby obtaining various AM extracts with enhanced antiviral activity.

Illustrative extraction processes according to various embodiments of the disclosure are discussed with reference to the flowchart depicted in FIG. 1. According to some embodiments of the present disclosure, the extract process comprises the step of extracting the *A. maxima* biomass in hot water to yield a crude extract (step 110). For example, the biomass may be first suspended in water (e.g., distilled water or double distilled water), which is then heated to approximately 80° C. to 120° C. for a period of time. For example, the suspension may be heated to about 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120° C. According to various embodiments, the heat extraction step 110 may last for at least one hour, e.g., 1, 1.5, 2, 2.5, 3, 3.5, or 4 hours. In some embodiments, the heat extraction time may be even longer.

The *A. maxima* biomass suitable for extraction include living *A. maxima* organisms taken out from the culture system. Alternatively, the *A. maxima* biomass may be dead *A. maxima* organisms, such as those has been dried (e.g., by freeze drying, air drying, or spray drying). According to some embodiments provided herein, the dried *A. maxima* biomass is suspended in double distilled water (d.d. water) to a concentration of 10% (w/v %). However, as could be appreciated by persons having ordinary skill in the art, the concentration of the biomass in the suspension may range from 1% (w/v %) to 30% (w/v %), such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% (w/v %).

The extraction process also comprises a step 120, in which the solid residues in the crude extract are removed. One common measure for removing solid residues is centrifugation. For example, the crude extract may be centrifuged at 1,000 to 5,000 rpm (e.g., 1,000, 1,500, 2,000, 2,500, 3,000, 3,500, 4,000, 4,500, or 5,000 rpm) for a sufficient time (such as, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 minutes).

After removing the solid residues from the crude extract, one may obtain the hot-water AM extract (for instance, the supernatant collected from the centrifugation tube). As discussed below, the hot-water extract (e.g., the SH extract according to working examples below) comprises an increased sugar content, as compared with conventional extracts prepared by cold-water extraction (FE-L-APO). Also, the protein level in hot-water extract is less that in the cold-water extract.

In optional embodiments, the aqueous hot-water extract may be dried to obtain hot-water extract powder. For example, the aqueous hot-water extract may be free-dried, spray-dried, or air-dried, or dried by any suitable or equivalent means.

As could be appreciated, both the hot-water extract in aqueous form and the dried hot-water extract powder are within the scope of the "*A. maxima* extract" in the present disclosure, and either can be used to prepare the nutraceutical or pharmaceutical composition described herein.

Next, in step 130, the hot-water extract (or the hot-water extract powder) is subjected to molecular size separation (step 130). For example, the hot-water extract may be filtrated with a semi-permeable membrane having a molecular weight cut-off (MWCO) of 100 KD, thereby separating the hot-water extract into a low-molecular weight fraction and a high-molecular-weight fraction. In this way, the high-molecular-weight fraction comprises an increased amount of constituents having a molecular weight of more than 100 KD, whereas the low-molecular weight fraction comprises more constituents having a molecular weight of less than 100 KD. Experimental data presented below show that the high-molecular-weight extract (e.g., the SH1 extract according to working examples below) elicits better antiviral efficacy, compared with the sugar-rich hot-water extract or the low-molecular-weight AM extract.

In the case where the hot-water extract powder is used as the starting material for the filtration, the hot-water extract powder is first mixed with appropriate amount (10- to 50-fold) of d.d. water before the filtration. For example, the water content may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 folds with respect to the weight of the dried hot-water extract powder.

The filtration process may be carried out per the manufacturer's instruction, and the operator may use his or her own discretion to decide whether certain modifications are required given the circumstances.

Like the hot-water extract discussed above, the high-molecular-weight extract may be dried to produce high-molecular-weight extract powder. The products in both the aqueous form and solid powder form are suitable for use as the AM extract described herein.

Then, in step 140, the constituents in the high-molecular-weight extract (or the high-molecular-weight extract powder) are further separated based on the charge of the molecules. According to embodiments of the present disclosure, the charge separation is carried out using the anion-exchange chromatography. For example, the anion-exchange chromatography may use the diethyl aminoethyl (DEAE)-based column, quaternary aminoethyl (QAE)-based column or a trimethylamino ethane (TMAE)-based column, or other positively-charged columns.

In some optional embodiments, the salinity of the high-molecular-weight extract (or a solution containing the high-molecular-weight extract powder) may be first adjusted to about 0.5 to 2.0% (e.g., 0.5, 0.6, 0.7, 0.8, 0.9, 1.0, 1.1, 1.2, 1.3, 1.4, 1.5, 1.6, 1.7, 1.8, 1.9, or 2.0%). The high-molecular-weight extract powder may be diluted in a way similar to that described above in connect ion with the hot-water extract powder. In some cases, the high-molecular-weight extract powder may be diluted by more than 50-fold, such as by 51, 52, 53, 54, 55, 56, 57, 58, 59, 60, 65, 70, 75, 80, 85, 90, 95, or 100 folds, or even higher.

Still optionally, the aqueous solution (with or without salinity adjustment) is further treated by centrifugation to remove the solid residues therefrom. For example, in some embodiments, the aqueous solution is centrifuged at 5,000 to 10,000 rpm (e.g., 5,000, 5,500, 6,000, 6,500, 7,000, 7,500, 8,000, 8,500, 9,000, 9,500, or 10,000 rpm) for a sufficient time (such as, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 minutes).

The anion-exchange chromatography may be carried out per the manufacturer's instruction, and of course, suitable modifications may be made as needed.

According to common chromatography practice, the column is first rinsed with suitable amount of d.d. water, and then the chromatography sample (i.e., the pre-treated aqueous AM extract) is allowed to run through the column, and the initial effluent is collected. Optionally, the column may be rinsed again with d.d. water, and the secondary effluent flowing through the column is also collected and combined with the initial effluent. The initial, secondary, and combined effluents are referred to, individually or collectively, as the AM extract rich in positively-charged and/or neutral polysaccharides, and the dried powder obtained from such AM extract is the extract powder rich in positively-charged or neutral polysaccharides.

Then, the column is eluted with a suitable volume of a salt solution (e.g., 1M NaCl); the elution collected in this step is the AM extract rich in negatively-charged polysaccharides, and the dried powder obtained from such AM extract is the extract powder rich in negatively-charged polysaccharides.

Some of the salts used or yields during the anion-exchange chromatography may be cytotoxic, and hence, in some optional embodiments, the AM extract rich in positively-charged and/or neutral polysaccharides and the AM extract rich in negatively-charged polysaccharides are subjected to another molecular size separation before being dried so as to remove the salts from the extract.

The experimental data below indicate that the AM extract rich in positively-charged and/or neutral polysaccharides (such as the SHD1 extract according to some working examples) is more potent in the antiviral activity than the high-molecular-weight extract (e.g., SH1 extract) or the AM extract rich in negatively-charged polysaccharides (such as the SHR1 extract according to some working examples) is.

As could be appreciated, the AM extract rich in positively-charged and/or neutral polysaccharides and the AM extract rich in negatively-charged polysaccharides, as well as the powder derived therefrom are within the scope of the AM extract of the present invention.

According to some embodiments of the present disclosure, the method comprises the step of administering to the subject an effective amount of the present AM extract so as to treat the viral infection or a disorder associated with the viral infection. In some cases, the virus replication in the subject may be substantially inhibited by the administered AM extract, thereby eradicating the viral infection in the subject.

As could be appreciated by persons having ordinary skill in the art, the effective amount may vary with many factors, such as the particular condition being treated, the severity of the condition, the individual patient parameters (including age, physical condition, size, gender and weight), the duration of the treatment, the nature of concurrent therapy (if any), the specific route of administration and like factors within the knowledge and expertise of the health practitioner. According to some embodiments of the present disclosure, the effective amount of the present AM extract is 0.01 to 1,000 mg/Kg body weight per day for a human subject, for example, 0.01, 0.02, 0.03, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1,000 mg/Kg body weight per day.

According to certain embodiments, the effective amount of the present AM extracts for treating EV infection is 0.375 to 125 mg/kg/day for mice; preferably 1 to 60 mg/kg/day; more preferably 3 to 30 mg/kg/day. For example, the daily dose for mice may be 0.375, 0.75, 1, 1.5, 2, 2.5, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, or 125 mg/kg.

According to certain embodiments, the subject is adult human, and the effective amount of the present AM extracts for treating EV infection is 0.01 to 10 mg/kg/day; preferably 0.8 to 4.8 mg/kg/day; more preferably 0.24 to 2.4 mg/kg/day. For example, the daily dose for a human subject may be 0.01, 0.02, 0.03, 0.04, 0.05, 0.06, 0.07, 0.08, 0.09, 0.1, 0.12, 0.15, 0.2, 0.24, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.4, 2.5, 3, 3.5, 3.6, 4, 4.5, 4.8, 5, 5.5, 6, 6.5, 7, 7.5, 8, 8.5, 9, 9.5, or 10 mg/kg. As could appreciated, human equivalent dose (HEQ) for the present AM extract or pharmaceutical composition comprising the same can be calculated by persons having ordinary skill in the art based on the animal doses provided in the working examples below. For example, one may follow the guidance for industry published by US Food and Drug Administration (FDA) entitled "Estimating the Maximum Safe Starting Dose in Initial Clinical Trials for Therapeutics in Adult Healthy Volunteers (July 2005)" in estimating a maximum safe dosage for use in human subjects. For example, the above-mentioned range of the effective amount for human subject is derived from the effective dosages for rats using the conversion factors provided in Table 1 of said FDA guidance, assuming 60 kg human.

The present AM extract may be administered via systemic (e.g., oral or i.p.) or topical (such as transmembrane or transmucosal) routes.

According to some embodiments of the present disclosure, the method comprises the steps of spraying to the air, or spraying the subject an effective concentration of the AM extracts so as to prevent, or treat the viral infection as disinfectants. The concentration of AM extracts in the formulation could be 1-100000 ug/ml.

According to some embodiments of the present disclosure, the method comprises the steps of spraying or patching, topically, to the subject an effective concentration of the AM extracts so as to treat the viral infection or a disorder associated with the viral infection such as herpes caused by HSV-1/2 or hand-foot-and-mouth diseases caused by enteroviruses. The formulation also would be a biocompatible material, comprising a biocompatible matrix, and AM extract distributed within the matrix or across the surface of the matrix, in the form of jelly or ointment. The concentration of AM extracts in the formulation could be 1-100000 ug/ml.

For example, the present AM extract can be formulated, together with a nutraceutically- or pharmaceutically-acceptable excipient, into a nutraceutical or pharmaceutical composition suitable for the desired mode of administration. Certain nutraceutical or pharmaceutical compositions prepared in accordance with the presently disclosed and claimed inventive concept(s) are single unit dosage forms suitable for oral administration to a patient. The present nutraceutical or pharmaceutical composition may be formulated into solid, semi-solid, or liquid forms. Examples of dosage forms suitable for the afore-mentioned route of administration include, but are not limited to, tablets, caplets, capsules, cachets, troches, lozenges, powders, solutions, dispersions, suspensions (e.g., aqueous or non-aqueous liquid suspensions, oil-in-water emulsions, or a water-in-oil liquid emulsions), and elixirs. As could be appreciated, these nutraceutical or pharmaceutical compositions are also within the scope of the present disclosure.

According to certain optional embodiments, examples of the nutraceutically- or pharmaceutically-acceptable excipient include but are not limited to, starch, cyclodextrin, maltodextrin, methylcellulose, carbomethoxy cellulose, and xanthan gum. Also, the present nutraceutical or pharmaceutical compositions may further comprise one or more of the following components: solvents, dispersion media, coatings, surfactants, antioxidants, preservatives (e.g., antibacterial agents, antifungal agents), isotonic agents, adhesion delaying agents, stabilizers, gels, binders, excipients, disintegration agents, lubricants, sweetening agents, flavoring agents, and dyes.

For the nutraceutical composition comprising the present AM extract, it may further comprise additional nutritional components, such as vitamins, minerals, fiber, fatty acids, or amino acids.

In various embodiments, the subject is a mammal, which may benefit from the treatment method of the present disclosure. As used herein, "mammal" refers to all members of the class Mammalia, including humans; primates (e.g., monkey and chimpanzee); domestic and farm animals, such as dog, cat, rabbit, pig, sheep, goat, cow, horse, and cattle; as well as zoo, sports or pet animals; and rodents, such as mouse, rat and guinea pig. In an exemplary embodiment, the patient is a human.

In some embodiments, the present method further comprises the step of administering to the subject an effective amount of an agent for treating or ameliorating the symptoms of the viral infection, prior to, concurrent with, or after the administration of the present AM extract.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

Comparative Example: Preparation and Composition Analysis of Cold-Water AM Extracts Dried *A. maxima* biomass (10 g) was suspended in d.d. water (100 ml) with agitation. The suspension was placed in a refrigerator below 0° C. for at least 8 hours so that the suspension was frozen into a piece of ice block. The ice block was than thawed under 0 to 37° C. and mild vibration or agitation so that the ice block melted slowly. The freezing and thawing processes were performed at least twice, and then the thawed suspension was centrifuged at a higher speed for 1 hour so as to remove the solid residues. The cold-water AM extract thus-obtained is referred to as FE-L-APO extract. The FE-L-APO extract was lyophilized to yield FE-L-APO powders for further analysis.

The cold-water FE-L-APO extract was analyzed to determine weight percent (wt %) of protein (Bio-rad protein assay reagent using bovine serum albumin (BSA) as standard), total sugar, (phenol-sulfric acid assay using glucose as standard), nucleic acid ($OD_{260}$ absorbance), water (determined by loss-on-drying), and ash (determined by incineration at 600° C. for 7 hours), and the respective result are presented in Table 1 (expressed as means±S.D. from three independent batches).

TABLE 1

Composition analysis of FE-L-APO extract

|  | Content (wt %) |
| --- | --- |
| Protein | 39.33 ± 5.6 |
| Total sugar | 11.79 ± 5.7 |
| Nucleic acid | 19.29 ± 2.7 |
| Water | 5 ± 1 |
| Ash | 1.2 ± 0.3 |
| Others | 23.39 |

The glycosyl composition of the FE-L-APO extract was determined by gas chromatography-mass spectrometry (GS-MC) analysis, and the results for three batches of the FE-L-APO extract were summarized in Table 2.

TABLE 2

Monosaccharide Composition of FE-L-APO extract (in molar percent, mol %)

|  | A5-S5 101105 | A5-S5 110309 | A5-S5 110427 |
| --- | --- | --- | --- |
| Fucose | 2.00 | 1.73 | 2.29 |
| Rhamnose | 25.72 | 18.19 | 26.57 |
| Galactosamine | n.a. | n.a. | n.a. |

TABLE 2-continued

Monosaccharide Composition of FE-L-APO extract (in molar percent, mol %)

|  | A5-S5 101105 | A5-S5 110309 | A5-S5 110427 |
|---|---|---|---|
| Arabinose | 1.33 | 0.87 | 1.13 |
| Glucosamine | 8.36 | 6.80 | 8.02 |
| Galactose | 6.62 | 7.49 | 5.83 |
| Glucose | 18.65 | 15.01 | 20.12 |
| Mannose | 54.41 | 46.02 | 56.32 |
| Xylose | 1.71 | 1.77 | 1.61 |

The FE-L-APO extract was further separated into fractions of Allophycocyanin (APC), C-phycocyanin (C-PC), FE-L-APO(H), and FE-L-APO (T). The APC and CPC fractions were protein fractions obtained by subjecting the FE-L-APO extract to further DEAE and HA column separation. FE-L-APO(H) and FE-L-APO(T) fractions were polysaccharide fractions. FE-L-APO(H) extract was prepared by the hot water extraction of FE-L-APO to denature the protein fraction and separate the protein fraction by centrifugation. The FE-L-APO(T) extract was prepared by denaturing the protein contents of the FE-L-APO extract with trichloroacetic acid, and then precipitated and separated the protein fraction with centrifugation.

Example 1: Preparation and Compositional Analysis of the Hot-Water AM Extracts

Dried *A. maxima* biomass (10 g) was suspended in d.d. water (100 ml) with agitation. The suspension was heated to about 80° C. to 120° C. for at least 1 hour, thereby obtaining a crude extract. The crude extract was centrifuged at 3,500 rpm for about 20 to 30 minutes, and the supernatant thus collected is the hot-water AM extract (SH extract). The aqueous SH extract was lyophilized to yield SH powder for further analysis.

For molecular size separation, the SH powder was dissolved in 10- to 50-fold d.d. water and then filtered with Amicon Ultra-15 Centrifugal Filter Unit using the Ultracel-100 membrane (MWCO: 100 KD). The retentate fraction (i.e., those retained within the sample side) was collected as the high-molecular-weight AM extract (SH1 extract), which lyophilized to give SH1 powder for subsequent use.

For charge separation, the DEAE gel (Sepharose™ Fast Flow) was used for anion-exchange chromatography. Briefly, the SH1 powder was dissolved in d.d. water with at least 50-fold dilution, and the salinity was adjusted to 0.8~1.0% by adding 0.4~0.5 g of NaCl into 50 mL of the diluent. The diluent was then centrifuged at 8,000 rpm for 30 minutes, and the supernatant was filtered with 1-μm mesh to remove impurities, thereby obtaining the sample solution ready for chromatography. DEAE column prepared using 200 ml DEAE gel was first equilibrated with 5 to 10 column volume (CV) of d.d. water. Thereafter, the sample solution (50 ml) was injected into the column at a flow rate of 4 ml/min, and the initial effluent lowing through the column was collected. Next, the column was rinsed with 500 mL of d.d. water, and the effluent running through the column was collected as the secondary effluent. The initial effluent and secondary effluent were combined to give the AM extract rich in positively-charged and/or neutral polysaccharides (SHD1 extract). After rinsing, the DEAE column was eluted with 1 to 3 CV of 1M NaCl, and the elution was collected, thereby obtaining the AM extract rich in negatively-charged polysaccharides (SHR1 extract).

The aqueous SHD1 and SHR1 extracts were then filtrated with Amicon Ultra-15 Centrifugal Filter Unit using Ultracel-100 membrane, respectively, to remove salts and other impurities therefrom. The retentate fractions were then lyophilized to obtain the SHD1 powder and SHR1 powder for further analysis.

The SH powder, SH1 powder, SHD1 powder, and SHR1 powder were subjected to a series of compositional analyses, including total sugar content (phenol-sulfric acid assay using the monosaccharide composition of AM extracts as standard), acid sugar content (m-hydroxydiphenyl method using glucuronic acid as standard), deoxy sugar (The Determination of Methylpentoses assay using rhamnose as standard), nucleic acid ($OD_{260}$ absorbance), total protein (Bio-rad protein assay reagent using BSA as standard); crude fat (A.O.A.C-960.39), water (determined by loss-on-drying), and ash (determined by incineration at 600° C. for 7 hours), and the respective result are presented in Table 3.

TABLE 3

Composition analysis of AM extracts (in percent by weight, wt %)

|  | SH | SH1 | SHD1 |
|---|---|---|---|
| Acidic sugar | 2.97 | 3.22 | 5.53 |
| Deoxy sugar | 8.53 | 10.73 | 27.03 |
| Total sugar | 29.52 | 31.59 | 61.05 |
| Nucleic acid | 19.54 | 18.77 | 4.98 |
| Protein (BIO-RAD) | 5.88 | 6.29 | 1.93 |
| Crude fat | trace | trace | trace |
| Water | 5~7 | 5~7 | 5~7 |
| Ash | No Test Result | No Test Result | No Test Result |

Figure 2A:
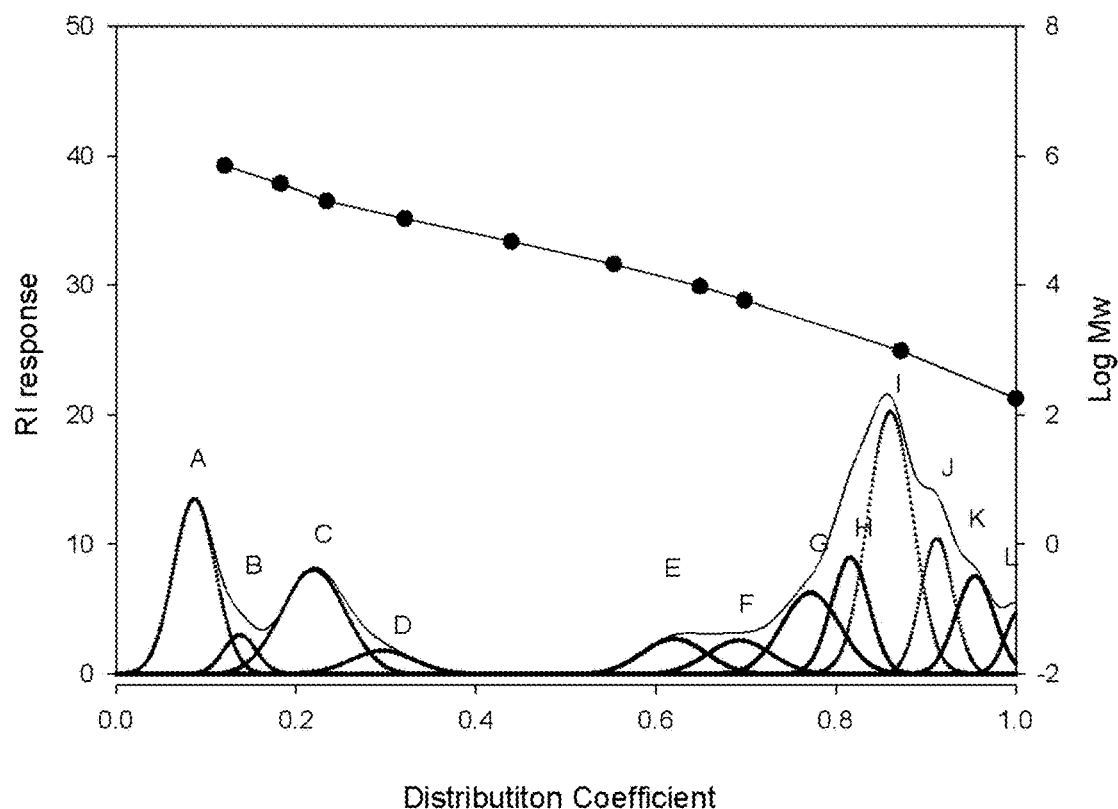
FIG. 2A to FIG. 2C are chromatographs showing the molecular weight distribution of polysaccharides in the present AM extracts according to one working example of the present disclosure.
Figure 2B:
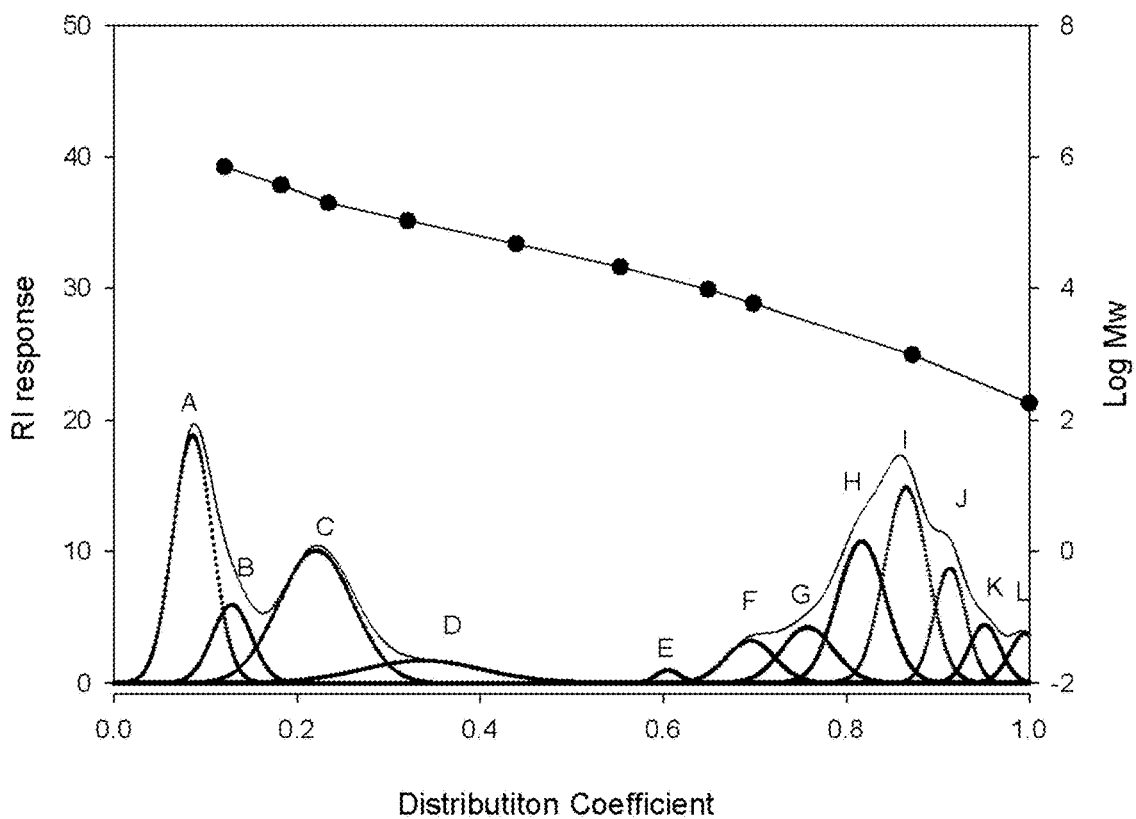
Figure 2C:
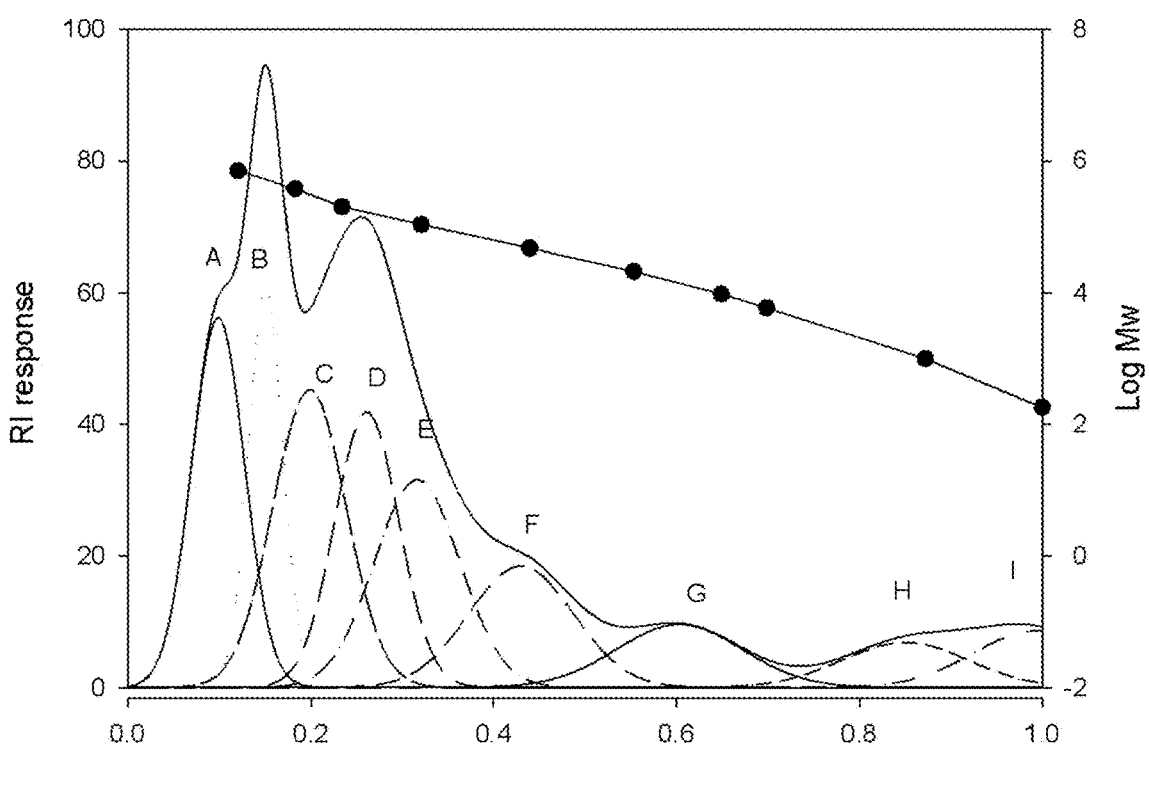

Further, high performance size exclusion chromatography (HPSEC) was utilized to separate the polysaccharides in the total sugar content, and then the molecular masses of their fractions were determined with refractive-index (RI) detection. Briefly, the polysaccharides were separated using TSK guard column PWH (7.5 mm×7.5 cm) coupled with TSK gel G4000PW column (7.5 mm×30 cm) and TSK gel G3000PW column (7.5 mm×30 cm). Columns were eluted at a flow rate of 0.5 mL/min with 0.3 N $NaNO_3$, containing 0.02% $NaN_3$. FIG. 2A, FIG. 2B, and FIG. 2C respectively show molecular weight distribution curve of polysaccharides in the SH extract, SH1 extract, and SHD1 extract, and quantitative results are summarized in Table 4 to Table 6.

TABLE 4

Molecular weight distribution of SH extract

| Peak | MW | DPw | Peak area percentage (%) |
|---|---|---|---|
| A | 1104367.8 | 6816.97 | 14.32 |
| B | 597417.5 | 3687.65 | 2.49 |
| C | 303789.7 | 1875.13 | 12.82 |
| D | 153091.2 | 944.90 | 2.85 |
| E | 13734.4 | 84.67 | 4.36 |
| F | 7683.3 | 47.32 | 4.16 |
| G | 3698.5 | 22.72 | 9.17 |
| H | 2182.2 | 13.36 | 8.47 |
| I | 1376.5 | 8.39 | 23.11 |
| J | 684.3 | 4.11 | 8.60 |
| K | 398.8 | 2.35 | 7.37 |
| L | 185.0 | 1.09 | 2.29 |

According to the data provided in FIG. 2A and Table 4, approximately two-third of the polysaccharides in the SH extract powder had a molecular weight of less than 100 KD. On the other hand, for the SH1 extract powder derived from the high-molecular-weight AM extract, polysaccharides with molecular weight greater than 100 KD account for almost half of the total sugar contents (see, FIG. 2B and Table 5).

TABLE 5

Molecular weight distribution of SH1 extract

| Peak | MW | DPw | Peak area percentage (%) |
|---|---|---|---|
| A | 1099926.5 | 6789.56 | 18.63 |
| B | 573379.5 | 4156.55 | 5.90 |
| C | 316191.0 | 1951.69 | 18.67 |
| D | 153105.0 | 944.98 | 5.10 |
| E | 14066.1 | 86.72 | 0.59 |
| F | 7131.0 | 43.91 | 4.00 |
| G | 4106.7 | 25.24 | 5.56 |
| H | 2256.0 | 13.81 | 13.06 |
| I | 1282.0 | 7.80 | 16.15 |
| J | 670.3 | 4.03 | 6.95 |
| K | 398.8 | 2.35 | 3.52 |
| L | 183.5 | 1.33 | 1.86 |

When the high-molecular-weight SH1 powder was further processed with the anion-exchange chromatography, the resultant fraction with predominantly positively-charged and neural polysaccharides possessed more high-molecular-weight polysaccharides. The data in FIG. 2C and Table 6 show that more than 75% of polysaccharides in the SHD1 extract powder had a molecular weight of greater than 100 KD.

TABLE 6

Molecular weight distribution of SHD1 extract

| Peak | MW | DPw | Peak area percentage (%) |
|---|---|---|---|
| A | 1023005.0 | 6314.73 | 16.23 |
| B | 523071.5 | 3228.73 | 11.32 |
| C | 393198.4 | 2427.04 | 18.04 |
| D | 206803.6 | 1276.45 | 14.66 |
| E | 143597.4 | 886.29 | 14.74 |
| F | 64782.8 | 399.78 | 10.56 |
| G | 20795.2 | 128.25 | 6.60 |
| H | 2946.0 | 18.07 | 4.64 |
| I | 787.0 | 4.75 | 3.21 |

The monosaccharide composition of present AM extracts was analyzed using high-performance anion-exchange chromatography with pulsed amperometric detection (HPAEC-PAD), and the respective result are presented in Table 7 (expressed as means±S.D. from three independent batches).

TABLE 7

Monosaccharide composition of AM extracts (in molar percent, mol %)

| | Fuc | Rha | Ara | Gal | Glc | Man | Xyl | Glc A |
|---|---|---|---|---|---|---|---|---|
| SH | 6.2 ± 0.4 | 40.4 ± 0.6 | 5.4 ± 0.3 | 8.5 ± 0.2 | 28.1 ± 0.4 | 4.4 ± 0.2 | 3.8 ± 0.3 | 3.1 ± 0.4 |
| SH1 | 7.2 ± 0.4 | 44.2 ± 1.5 | 4.7 ± 0.1 | 7.6 ± 0.2 | 25.3 ± 0.7 | 4.0 ± 0.4 | 3.0 ± 0.4 | 3.9 ± 0.2 |
| SHD1 | 8.3 ± 0.5 | 59.1 ± 2.7 | 4.4 ± 0.4 | 7.2 ± 0.6 | 12.1 ± 1.1 | 1.1 ± 2.0 | 1.2 ± 0.7 | 6.6 ± 1.1 |

Fuc: fucose,
Rha: rhamnose,
Ara: arabinose,
Gal: Galctose,
Glc: glucose,
Man: mannose, and
Glc A: glucuronic acid.
Gal A, galacturonic acid, was not detectable is all samples.

The data in Table 7 indicate that the most abundant monosaccharide in the three hot-water AM extracts according to the present invention was rhamnose, which accounted for about 40 to 60 mol % based on the total monosaccharides. In contrast, the data in Table 2 show that the in the extract prepared using cold-water extraction, the most abundant monosaccharide is mannose (about 46 to 56 mol %), with rhamnose being the second (about 18 to 27 mol %). On the other hand, mannose only constitute a minor portion (less than 5 mol %) of the present, hot-water extraction-based AM extracts.

SHD1 extract powder was further subjected to glycosyl linkage analysis. Briefly, after the sequence of permethylation, hydrolysis, reduction with $NaBD_4$, and acetylation, the glycosyl linkage was elucidated using the GC-MS spectrum and the retention index on a HP5-MS column of the resulting O-methylated alditol acetates product was recorded. The results are summarized in Table 8.

The data in Table 8 indicate that the most significant glycosyl linkage is the 3-rhap linkage (32.59%), followed by 4-rhap (14.76%) and 2,3-rhap (6.12%). Together, the top three glycosyl linkages account for more than half of the glycosyl linkages.

TABLE 8

Glycosyl linkage of SHD1 extract

| | Linkage | Sugar Composition (%) | Peak area (%) |
|---|---|---|---|
| Fucose | T-fucp | 8.9 | 4.28 |
| | 3-fucp | | 3.33 |
| | 2,3-fucp | | 1.28 |
| Rhamnose | 2-rhap | 63.3 | 4.89 |
| | 3-rhap | | 32.59 |
| | 4-rhap | | 14.76 |
| | 2,3-rhap | | 6.12 |
| | 3,4-rhap | | 4.92 |
| Arabinose | 3-arap | 4.7 | 4.7 |
| Galactose | T-galp | 7.7 | 6.19 |
| | 6-galp | | 0.87 |
| | 2,6-galp | | 0.66 |
| Glucose | T-glcp | 13.0 | 1.06 |
| | 2-glcp | | 1.65 |
| | 4-glcp | | 1.97 |
| | 6-glcp | | 5.36 |
| | 4,6-glcp | | 2.92 |
| Mannose | | 1.2 | |
| Xylose | | 1.3 | |

Figure 3A:
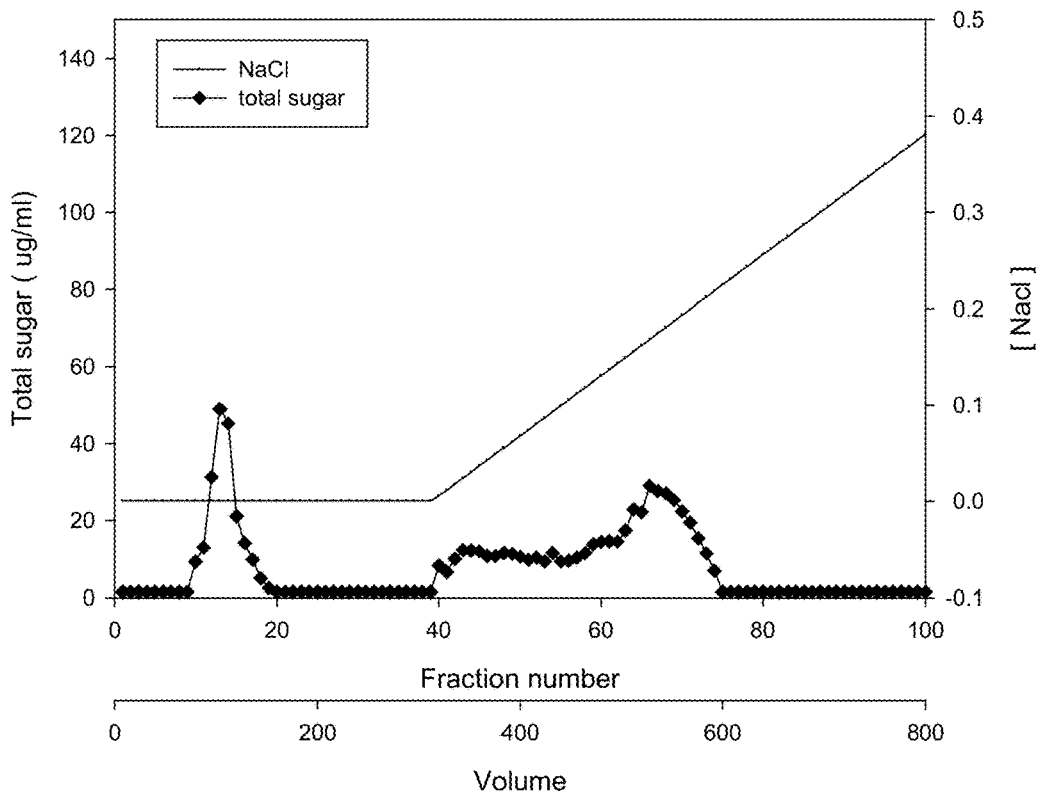
FIG. 3A and FIG. 3B are chromatographs showing charge of the composition components in the present AM extracts according to one working example of the present disclosure.
Figure 3B:
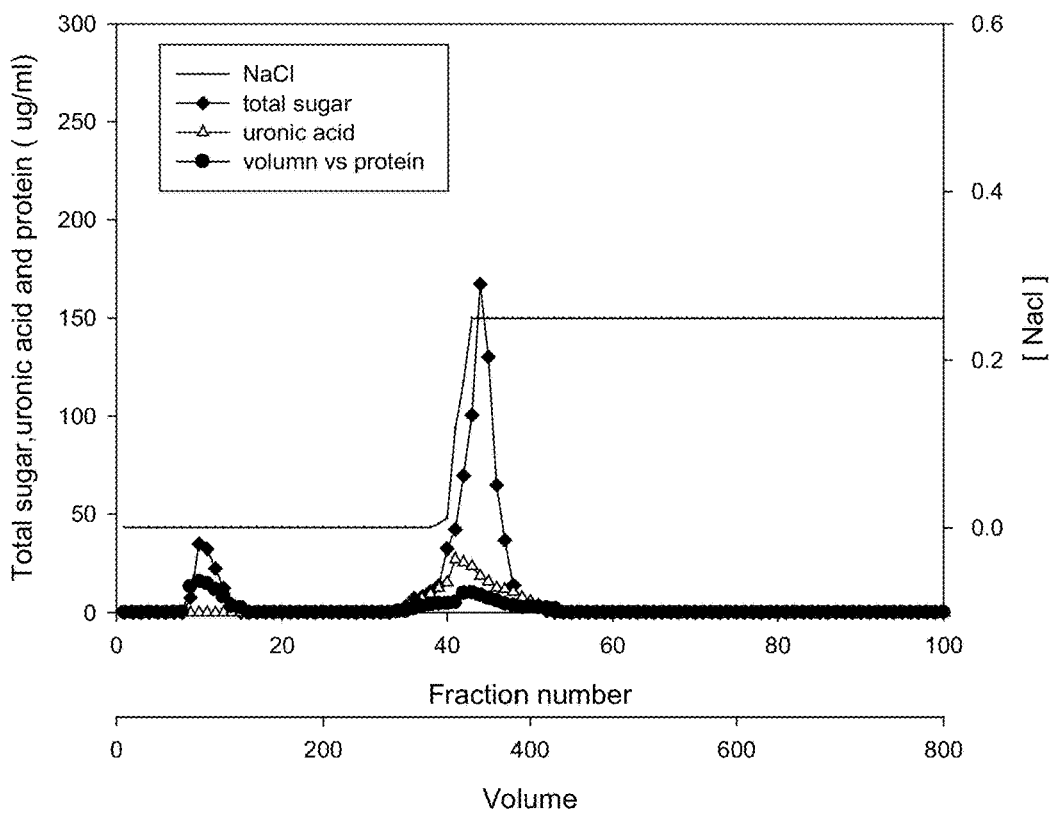

The SHD1 powder was again subjected to the DEAE column chromatography to further separate the components therein based on their charge density. Results are provided in the chromatographs of FIG. 3A (the total sugar content) and FIG. 3B (Weight (%) to SHD1, the contents of uronic acid to all sugar). Composition analysis of the effluent and elution from the chromatography were analyzed as described above, and the results are summarized in Table 9.

TABLE 9

Composition analysis of DEAE fractions of SHD1 extract

| Fraction | W to SHD1 (%) | Uronic acid (%) |
|---|---|---|
| SHD1-Effluent | 22.8% | nd |
| SHD1-Elution | 77.2% | 29.85 |

Example 3: Antiviral Activity of AM Extracts Against Enterovirus

The antiviral efficacy and the cytotoxicity of the AM extracts was investigated by the neutralization test and MTT assay, respectively. Results are expressed as means±SD from four wells, unless specified otherwise.

RD cells were grown in Dulbecco's Modified Eagles's Medium (DMEM), supplemented with 10% fetal bovine serum (FBS). EV71/TWN/4643/1998 was obtained from Jen-Ren Wang, National Cheng Kung University (Tainan, Taiwan); EV71/CA/BrCr/1970, the prototype of EV71 (ATCC Accession No.: VR 784), was obtained from the ATCC. EV71/TWN/1743/1998 and TWN/2231/1998.

For neutralization test, the inhibition of the cytopathic effect induced by Enteroviruses on RD cells was measured. Monolayer of RD cells in 96-well plates (6,000 cells/well) were infected with EV71 viruses and were treated with serial concentrations of the AM extracts. For adhesion, cells were incubated at 37° C. for 1 hour; following adsorption, the infected cell plates were overlaid with 50 µl of DMEM at 37° C. for 48 hours. Then, the plates were fixed by adding 100 µl of 0.5% formaldehyde for 1 hour at room temperature. Thereafter, the formaldehyde was removed and the sample was stained with 0.1% crystal violet for 15 minutes at room temperature. Plates were washed and dried, and the density of cells in each well was measured at 570 nm. The concentration required for the AM extract to reduce the virus-induced cytopathic effect by 50% relative to the virus only negative control was expressed as 50% effective dose ($EC_{50}$).

For MTT assay, RD cells were seeded in 96-well microplates (30,000 cells/well), and cultured in a humidified incubator for 24 hours. Culture media were then replaced with media containing the AM extracts at concentrations ranging from 0.048 to 50 mg/ml. A negative control group cultured in DMEM without the AM extract, and a blank group containing neither cells nor culture media, were also included. Cells were incubated for 72 hours, after which the culture medium was discarded and 20 µl of 3-(4,5-dimethylthiazol-2-yl)-2,5-diphenyltetrazoliumbromide (MTT) solution (1 mg/mL in DMEM) was added to each well. Cells were incubated for an additional 4 hours, and the MTT solution was then removed. Subsequently, 200 µl of 0.04N HCl in isopropanol was added to each well to dissolve the formazan crystals. Plates were then read on a microplate reader (BIOtAK, Bristol, UK) at 570 nm ($OD_{570}$). $CC_{50}$, the concentration resulting in 50% cell death compared with untreated controls was calculated according to the Reed-Muench method.

Summarized below in Table 10 are the $EC_{50}$ and $CC_{50}$, as well as the selectivity index (SI), the ration of $CC_{50}$ to $EC_{50}$, of the present AM extracts and the cold-water extract.

TABLE 10

Antiviral activity of AM extracts against EV71/TW/4643/1998

| Samples | $EC_{50}$ (µg/ml) | $CC_{50}$ (µg/ml) | SI |
|---|---|---|---|
| FE-L-APO | 76 ± 0 | >25000 | >329 |
| SH | 21 ± 3 | >25000 | >1190 |
| SH1 | 8 ± 0 | >25000 | >3125 |
| SHD1 | 3 ± 0.15 | >25000 | >8333 |
| SHR1 | 13 ± 089 | >25000 | >1923 |

The data in Table 10 demonstrate that the AM extracts according to the present disclosure (e.g., SH, SH1, SHD1, and SHR1 extracts) exhibited a better antiviral efficacy, as evidenced by the significantly lower $EC_{50}$ values, compared with the conventional FE-L-APO extract. With reference to the composition analyses presented above in the Comparative Example and Example 1, it is speculated that the antiviral activity of the present AM extracts comes largely from the polysaccharide contents therein. Comparison of the antiviral activities between the SH and SH1 extracts further reveals that the polysaccharide contents having a higher molecular weight (e.g., greater than 100 KD) seems to be more effective in inhibiting viral infection. Also, neutral and positively-charged polysaccharide contents are even more potent in view of its lowest $EC_{50}$ value among all tested groups.

It should be noted that although the $EC_{50}$ value of SHR1 extract having predominantly negatively-charged polysaccharides is higher than that of the SH1 extract and the SHD1 extract, it is lower than that of the SH extract. These results once more suggest that the polysaccharides having a higher molecular weight (e.g., greater than 100 KD) is more effective in protecting the host cells against the EV infection. In the other hand, our results also indicate that the fraction containing mostly low-molecular-weight components (e.g., molecules having a molecular weight less than 100 KD) exhibited no antiviral activity against EV71 (data not shown).

Moreover, the data in Table 10 indicate that all present AM extracts are highly selective toward the EV virus but not the RD cells with a selective index of more than 1,000, suggesting that such AM extracts are not cytotoxic at their effective dosage.

The SHD1-effluent fraction and SHD1-elution fraction prepared above were also subjected to the neutralization test to determine their antiviral efficacy. The results from two replicates are summarized in Table 11. The data in Table 11 suggest that when the components in the SHD1 extract were further separated based on their surface charge density, the fraction with predominantly the positively-charged and neutral components (SHD1-effluent) was more effective in protecting the host cells against EV infection than the fraction having mostly the negatively-charged components (SHD1-elution) did. On the other, since most components in the SHD1-elution have a molecular weight of greater than 100 KD (because this fraction was derived from the SH1 and SHD1 extracts), the $EC_{50}$ value of SHD1-elution was lower than that of the SH extract.

TABLE 11

Antiviral activity of AM extracts against EV71/TW/4643/1998

| Samples | $EC_{50}$ 1 (µg/ml) | $EC_{50}$ 2 (µg/ml) | $EC_{50}$ (µg/ml) |
|---|---|---|---|
| SHD1 | 2.82 | 2.39 | 2.61 ± 0.30 |
| SHD1-Effluent | 2.24 | 2.61 | 2.43 ± 0.26 |
| SHD1-Elution | 14.51 | 16.42 | 15.47 ± 1.35 |

The clinical symptoms of enterovirus infections at the early stage of the infection include HFMD and herpangina. Said symptoms are common to the infections caused by other enteroviruses. Therefore, it is desirable to provide an antiviral AM extract with a broad spectrum of anti-enterovirus efficacy. Other than the EV71/4643, we also evaluated the anti-viral efficacy of the SHD1 extract on EV71/CA/BrCr/1970 (Genotype A), EV71/TWN/1743/1998 (Genotype B), EV71/TW/2231/1998 (Genotype C), Coxsackie A6, Coxsackie A10, Coxsackie A16, Coxsackie B3, Influenza virus, Herpes simplex virus type 1 and type 2 (HSV-1, HSV-2) with neutralization test, and the results are summarized in Table 12 (expressed as means±S.D. from three independent replicates). Coxsackieviruses A6, A10, A16, B3, HSV-1 and HSV-2 were isolated from clinical specimens in the ClinicalVirology Laboratory of Chang Gung Memorial Hospital (Linkou, Taiwan).

TABLE 12

Antiviral activity of SHD1 extract against various viruses

| Virus | $EC_{50}$ (µg/ml) | $CC_{50}$ (µg/ml) | SI |
|---|---|---|---|
| EV71/BrCr (genotype A) | 27 | >25000 | >925.9 |
| EV71/1743 (genotype B) | 14 | >25000 | >1785.7 |
| EV71/2231 (genotype C) | 13 | >25000 | >1923.0 |
| EV71/4643 (genotype C) | 3 ± 0.15 | >25000 | >8333 |
| Coxsackie A6 | >1000 | >25000 | N/A |
| Coxsavkie A10 | 5.72 ± 0.14 | >25000 | >4370 |
| Coxsackie A16 | 1.31 ± 0.05 | >25000 | >19083 |
| Coxsackie B3 | 667 ± 9 | >25000 | >37.4 |
| Influenza A/WSN/33 | 333 ± 77 | >25000 | >75 |
| HSV-1 | 21.37 ± 1.82 | >25000 | >1170 |
| HSV-2 | 2.21 ± 0.04 | >25000 | >11312 |

The data in Table 12 indicate that except the present SHD1 exhibited satisfactory inhibitory efficacy and selectivity toward various strains of EV viruses. Also, the present SHD1 extract is quite effective in inhibiting the Coxsackie A10, Coxsackie A16, HSV-1, and HSV-2. It should be noted that the $EC_{50}$ values of SHR1 against HSV-1 (86.58±11.91 µg/ml) and HSV-2 (10.03±0.54 µg/ml) are higher than that of the SHD1, suggesting that the SHD1 extract is more effective in inhibiting the viral infection of HSV-1 and HSV-2. Also, the $EC_{50}$ of SHD1 extract against the Coxsackie B3 and Influenza A/WSN/33 was also acceptable.

To determine the possible stage(s) of viral life cycle targeted by the present AM extracts, time-of-addition and time-of-removal assays were performed.

Figure 4A:
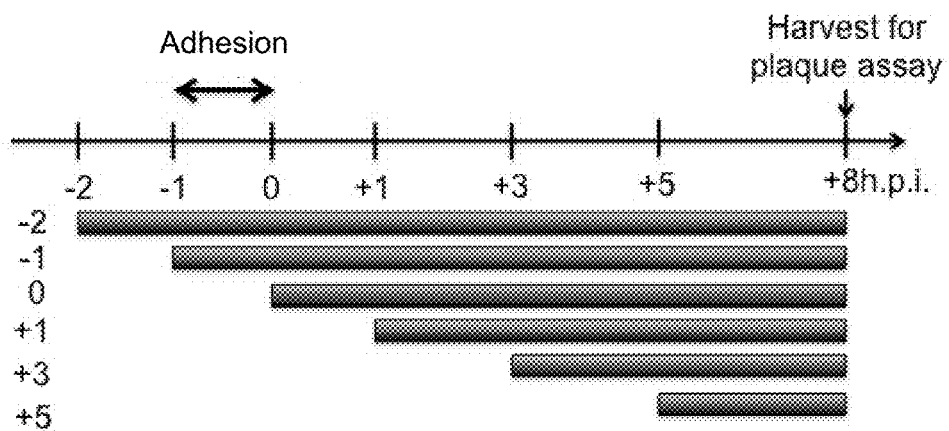
FIG. 4A and FIG. 4B show the scheme and results for time-of-addition assay according to one working example of the present disclosure.
Figure 4B:
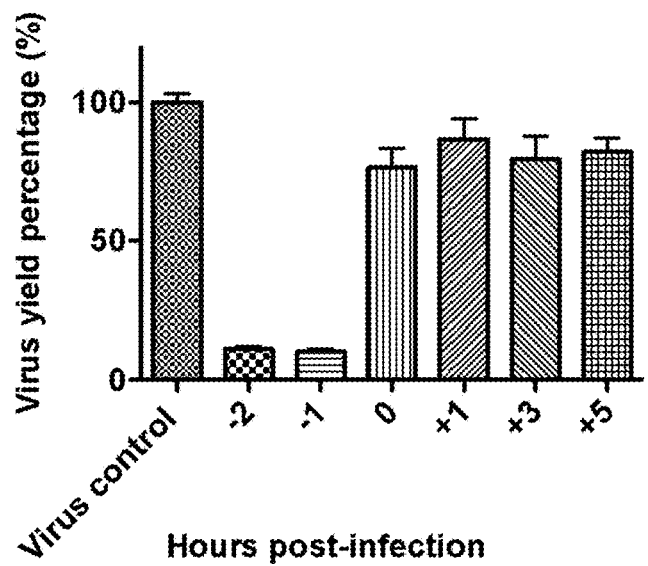

For the time-of-addition assay (see, FIG. 4A), at time point −1, RD cells in 6-well plates were contacted with EV71/TW/4643/1998 virus (multiplicity of infection (MOI)=2) and allowed for one-hour of adhesion, and the time point "0" was designated as the infection time. The RD cells were treated with 6 µg/ml of SHD1 extract at indicated interval. Supernatants and pellets were harvested 8 hours post-infection, and virus yields were determined by a plaque assay. The results, as summarized in FIG. 4B indicate that the SHD1 extract significantly inhibited the virus replication at the early stage of virus infection. When the SHD1 extract was added 2 hours (time point −2) and 1 hour (time point −1) before infection, the SHD1 could abate 89% and 90% of the virus yields compared to the virus control. On the other hand, for SHD1 extract added at the time of infection (time point 0) and 1-, 3-, and 5-hour post-infection, the inhibition efficacy of each group was only 24%, 13%, 11%, and 18%, respectively.

Figure 4C:
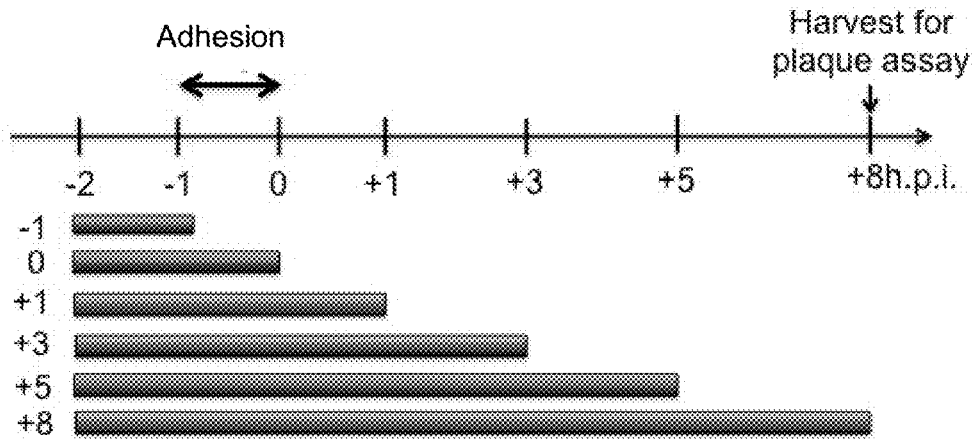
FIG. 4C and FIG. 4D show the scheme and results for time-of-removal assay according to one working example of the present disclosure.
Figure 4D:
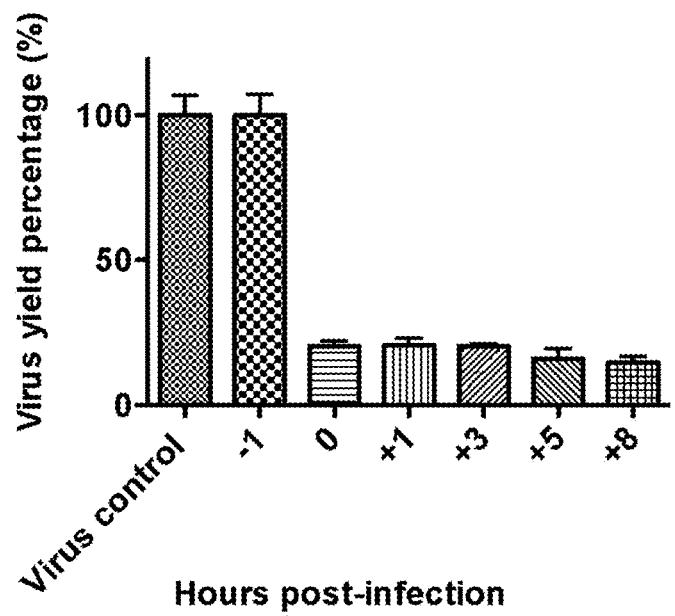

For the time-of-removal assay (see, FIG. 4C), 6 µg/ml of SHD1 were added before the cells were infected. The AM extracts were then removed at indicated intervals by replacing the culture medium with fresh E2 medium. Cells were harvested after 8 hours and virus yields were also determined by plaque assay. The results are summarized in FIG. 4D. According to FIG. 4D, when the SHD1 extract was removed at time point −1 (e.g., before the virus adhesion), the virus yield was 114% relative to the virus control. On the other hand, when the SHD1 extract was removed at time points "0", "+1", "+3", and "+5", the virus yields were only 20%, 20%, 20%, and 16%, respectively.

Taken together, these results suggest that the present AM extract (e.g., SHD1 extract) presented a significant inhibitory effect on the early stage of EV infection.

The following assay was carried out to further elucidate whether the inhibitory effect of the present AM extract comes from acting on the EV virus directly (for example, eliminate the virus itself) or acting on the early infection process (e.g., interfering the interaction between the virus and the host cells).

During an initial phase, 1×10$^5$ P.F.U. of EV71/TW/4643/1998 was mixed with 24 µg/ml of SHD1 extract or without the SHD1 extract for three hours under room temperature. Then, in the second phase, the mixtures were diluted by 10,000-fold before the plaque assay.

Figure 4E:
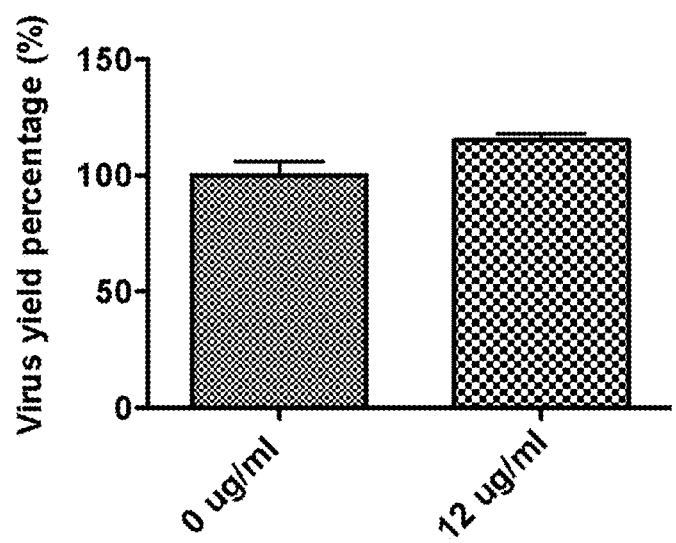
FIG. 4E shows the results of plaque forming assay according to one working example of the present disclosure.

The results, as summarized in FIG. 4E indicate that in the SHD1-treated group, the virus yield was 114% relative to the control group that was not treated with the SHD1 extract. As could be appreciated, in the SHD1-treated group, the virus was first treated with SHD1 extract at a concentration (24 µg/ml) that was higher than the $EC_{50}$ of the extract (~2-3 µg/ml), and after the dilution, the concentration of the SHD1 extract was way lower than its $EC_{50}$. Therefore, should it be case that the SHD1 extract acted directly on the EV virus itself, there would be significantly less virus yield in the treatment group, because most virus would lose their infective ability upon the initial treatment of high-dose SHD1 extract. However, the plaque assay results suggest otherwise. The significant viral yield observed in the SHD1-treated group indicate that the SHD1 extract did not act on the EV virus itself.

Judging from the plaque-forming ability in SHD1-treated group after dilution and in view of the results from the time-of-addition and time-of-removal assays, it is more likely that the present AM extract may interfere with the early process of viral infection, such as the attachment or adhesion steps.

Example 4: Therapeutic Efficacy of SHD1 on EV71/MP4 Infected ICR Mice

At day 0, 10-days old ICR mice were inoculated with EV71/MP4 (3.0×10$^6$ PFU/mouse) via i.p. route. One hour after the inoculation, the mice were administered with 0.375, 0.75, 1.5, or 3 mg/kg/day of SHD1 extract via i.p. injection or orally administered with 1, 5, or 50 mg/kg/day of SHD1 extract once daily for 10 consecutive days. The clinical scores and survival rate were monitored for 15 days (from day 0 to day 14); results were summarized in FIG. 5A (for i.p. injection of SHD1 extract) and FIG. 5B (for oral administration of SHD1 extract). The Clinical scores of "0" means healthy, "1" means weakness, "2" means paralysis of one leg, "3" means paralysis of two legs, and "4" means death.

Figure 5A:
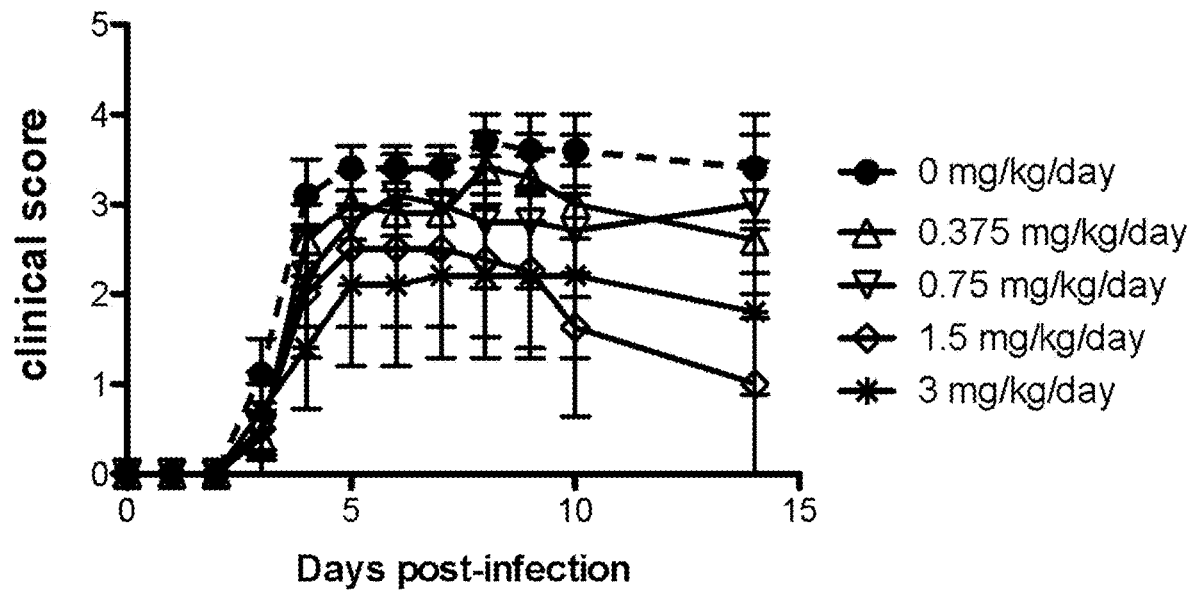
FIG. 5A and FIG. 5B show the therapeutic efficacy of SHD1 on EV71/MP4 infected ICR mice according to one working example of the present disclosure.
Figure 5B:
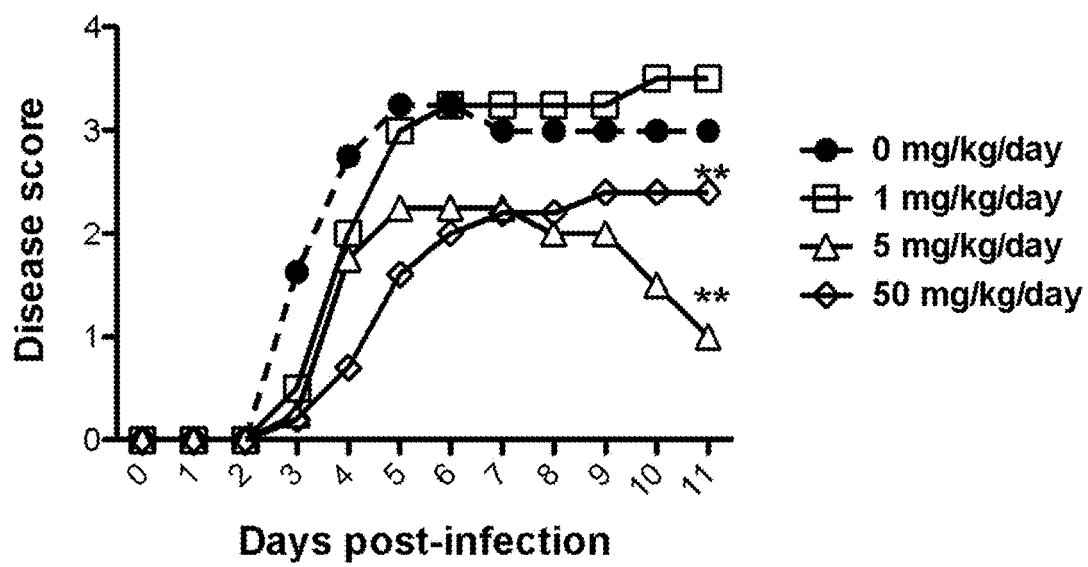

The data in FIG. 5A demonstrate that mice treated with 1.5 or 3 mg/kg/day of SHD1 extract manifested a better clinical score, as compare with vehicle-treated control mice. On the other hand, for the oral administration group, mice given 5 mg/kg of SHD1 extracts showed mild improvement over the vehicle-treated mice, whereas a significant improvement was seen in mice treated with 50 mg/kg of SHD1 extract. Also, there was no significant dose-dependent response regarding the therapeutic efficacy for the tested dosage.

Example 5: Antiviral Activity of AM Extracts Against Respiratory Syncytial Virus The antiviral activity ($EC_{50}$) of the present AM extract against RSV virus was investigated using the primary cytopathic effect (CPE) reduction assay using the MA-104 cells as the host cells. $CC_{50}$ was determined using Neutral red (NR)-based In vitro Toxicology assay.

The data summarized in Table 13 indicate that the present SH1 extract was 3.55-time more protective against the RSV infection.

TABLE 13

Antiviral activity of AM extracts against RSV

| Samples | EC$_{50}$ (μg/ml) | CC$_{50}$ (μg/ml) | SI |
|---|---|---|---|
| FE-L-APO | 611 ± 8 | >10000 | >59 |
| SH1 (SP-100KD) | 211 | >10000 | >476 |
| SHR1 | 325 ± 10 | >10000 | >30 |
| SHD1 | 91.5 ± 5.5 | 10000 | >109 |

Example 6: Antiviral Activity of AM Extracts Against Ebola Virus

The anti-Ebola activity (EC$_{50}$) of the present AM extract was determined using the plaque reduction assay using the Vero CCL81 cells as the host cells; CC$_{50}$ was determined using Neutral red (NR)-based In vitro Toxicology assay. In this example, the conventional FE-L-APO extract and Favipiravir, an antiviral agent, were used as controls.

The results, as summarized in Table 14, reveal that the SH1 extract inhibited the infection of Ebola virus at an EC$_{50}$ of 500 μg/ml, with a selective index of greater than 20, and the EC50 of FE-L-APO on Ebola virus is 270, with a selective index of greater than 37.

TABLE 14

Antiviral activity of AM extracts against Ebola virus/Zaire

| Samples | EC$_{50}$ (μg/ml) | CC$_{50}$ (μg/ml) | SI |
|---|---|---|---|
| FE-L-APO | 270 | >10000 | >37 |
| SH1 (SP-100KD) | 500 | >10000 | >20 |
| Favipiravir (positive control) | 96 μM | >1000 μM | >10 |

To further elucidate the relationship between the anti-Ebola activity and the fraction components of the AM extracts, the Ebola-infected CellTiter96 (MTS) cells treated with the Allophycocyanin (APC), C-phycocyanin (C-PC), FE-L-APO(H), and FE-L-APO (T) fractions from the FE-L-APO extract, and the SHD1 and SHR1 fractions from the SH1 were subjected to virus yield reduction assay using real-time polymerase chain reaction.

The data as summarized in Table 15 indicate that the Allophycocyanin fraction was most effective in inhibiting Ebola infection among the four FE-L-APO fractions. On the other hand, the EC$_{50}$ of the SHD1 was significantly lower than that of the SHR1. Moreover, both the SHR1 and SHD1 fractions were more effective in inhibiting Ebola infection than the four FE-L-APO fractions are.

The data also show that the SHD1 and SHR1 extracts achieved the EC$_{90}$ (in which the viral replication is inhibited by 90%) at 9.99 μg/ml and 30.4 μg/ml, respectively. In contrast, the EC$_{90}$ for all FE-L-APO fractions were greater than 400 μg/ml.

TABLE 15

Antiviral activity of further fractions against Ebola virus/Zaire

| Samples | EC$_{50}$ (μg/ml) | EC$_{90}$ (μg/ml) | CC$_{50}$ (μg/ml) | SI | SI$_{90}$* |
|---|---|---|---|---|---|
| Allophycocyanin | 1.77 | >400 | >400 | >226 | — |
| C-phycocyanin | 242 | >400 | >400 | >2 | — |

TABLE 15-continued

Antiviral activity of further fractions against Ebola virus/Zaire

| Samples | EC$_{50}$ (μg/ml) | EC$_{90}$ (μg/ml) | CC$_{50}$ (μg/ml) | SI | SI$_{90}$* |
|---|---|---|---|---|---|
| FE-L-APO (H) | 149 | >400 | >400 | >3 | — |
| FE-L-APO (T) | >400 | >400 | >400 | — | — |
| SHD1 | 1.35 | 9.99 | >400 | >296 | >40 |
| SHR1 | 9.1 | 30.4 | >400 | >44 | >13 |
| E64D (positive control) | <1.26 μM | 5.69 μM | >400 μM | >317 | >70 |

*SI90: selectivity index, a ratio of CC50 to EC90.

Example 7: Antiviral Activity of AM Extracts Against Porcine Epidemic Diarrhea Virus This example investigated the inhibitory activity of the AM extract against the porcine epidemic diarrhea virus (PEDV). In this example, the AM extract was first mixed with the virus. Specifically, DMEM (50 μl/well), 50 μl of FE-L-APO (2 mg/ml) or SH (20 mg/ml), and 100 μl/well of PEDV viral solution containing 1,000 PFU, 100 PFU, or 10 PFU were sequentially added into each well of a 96-well plate. For the positive control, 100 μl/well DMEM was mixed with 100 μl/well of different viral concentrations, whereas for the negative control, 200 μl of DMEM was used. The plate was then incubated at 37° C. for 60 minutes. Thereafter, the mixture (200 μl) from each well was added into each well of a 96-well plate containing Vero cells (1×10$^5$ cells/well) that had been were cultured overnight. The plate was then incubated at 37° C. for 5 days. The primary cytopathic effect was measured and the results are summarized in Table 16.

The results (from three replicates) show that the cells could not inhibit the formation of virus plaques in the presence of FE-L-APO at 1,000 PFU, 100 PFU, 10 PFU virus. On the other hand, the SH extract significantly reduced the PEDV virus plaques in Vero cells by 55-75%, relative to the positive control.

TABLE 16

Porcine epidemic diarrhea virus inhibition test

| | PFU | | |
|---|---|---|---|
| | 1,000 | 100 | 10 |
| FE-L-APO | 1002 | 102 | 13 |
| | 1010 | 104 | 12 |
| | 1006 | 105 | 9 |
| SH | 450 | 34 | 5 |
| | 467 | 25 | 3 |
| | 462 | 30 | 4 |
| Positive control | 1002 | 100 | 9 |
| | 1005 | 103 | 12 |
| | 998 | 102 | 11 |
| Negative control | 0 | 0 | 0 |

Example 8: Antiviral Activity of AM Extract Against Porcine Reproductive and Respiratory Syndrome Virus In this test, the inhibitory activity of the present AM extract against porcine reproductive and respiratory syndrome virus (PRRSV) was investigated. In this example, the AM extract was first mixed with the host cells. Briefly, the Vero cells (1×10$^5$ cells/well) were cultured in 96-well plates overnight. Thereafter, 50 μl of FE-L-APO (2 mg/ml) and SH (20 mg/ml) were added into each well, and the plate was at 37° C. for 60 minutes. Then, PRRSV viral solution (100 μl/well) containing 1,000 PFU, 100 PFU, or 10 PFU was added into each well. For the positive control, 100 μl/well DMEM was mixed with 100 μl/well of different concentrations of virus, whereas for the negative control, 200 μl of DMEM was used. The plate was then incubated at 37° C. for 5 days, and the primary cytopathic effect was measured daily.

The results (from three replicates), as summarized in Table 17, indicate that when the cells were infected with 1,000 PFU of PRRSV before the addition of the extract, neither the FE-L-APO extract nor the SH extract could effective inhibit the viral infection. However, for cells infected with 100 PFU of PRRSV, the present SH extract protected more than 90% of the host cells from the PRRSV infection.

TABLE 17

Porcine reproductive and respiratory syndrome virus inhibition test I

| | PFU | | |
|---|---|---|---|
| | 1000 | 100 | 10 |
| FE-L-APO | 1001 | 20 | 1 |
| | 1020 | 18 | 2 |
| | 1012 | 28 | 1 |
| SH | 998 | 6 | 7 |
| | 995 | 5 | 6 |
| | 1003 | 3 | 9 |
| Positive control | 1003 | 105 | 10 |
| | 1005 | 102 | 12 |
| | 1003 | 106 | 9 |
| Negative control | 0 | 0 | 0 |

In this test, the AM extract was first mixed with the PRRSV. Briefly, the AM extract was first mixed with the virus. Specifically, DMEM (50 μl/well), 50 μl of FE-L-APO (2 mg/ml) or SH (20 mg/ml), and 100 μl/well of PRRSV viral solution containing 1,000 PFU, 100 PFU, or 10 PFU were sequentially added into each well of a 96-well plate. For the positive control, 100 μl/well DMEM was mixed with 100 μl/well of different viral concentrations, whereas for the negative control, 200 μl of DMEM was used. The plate was then incubated at 37° C. for 60 minutes. Thereafter, the mixture (200 μl) from each well was added into each well of a 96-well plate containing Vero cells ($1 \times 10^5$ cells/well) that had been were cultured overnight. The plate was then incubated at 37° C. for 5 days. The primary cytopathic effect was measured and the results are summarized in Table 18.

The results demonstrate that when the virus was pre-treated with the present SH extract, the viral infection efficacy was reduced by about 50%, even when the cells were infected with high concentration of PRRSV viruses (e.g., 1,000 PFU). Also, when the cells were infected with lower concentrations of PRRSV (e.g., 100 or 10 PFU), a total inhibition of the PRRSV infection was achieved.

TABLE 18

Porcine reproductive and respiratory syndrome virus inhibition test II

| | PFU | | |
|---|---|---|---|
| | 1,000 | 100 | 10 |
| FE-L-APO | 679 | 0 | 0 |
| | 691 | 0 | 0 |
| | 698 | 0 | 0 |
| SH | 510 | 0 | 0 |
| | 520 | 0 | 0 |
| | 493 | 0 | 0 |
| Positive control | 1004 | 106 | 8 |
| | 1007 | 104 | 12 |
| | 999 | 101 | 11 |
| Negative control | 0 | 0 | 0 |

Example 9: Antiviral Activity of AM Extract after Digestive Enzymes Treatment

In this example, the present AM extract was treated with digestive enzymes, and the $EC_{50}$ was determined to elucidate whether the AM extract would loss its antiviral activity upon being ingested orally.

The SH powder was dissolved in d.d. water at room temperature, and the pH was adjusted to 6. α-amylase (100 μl/1 g sample) was added to the SH solution in 95° C. water bath (shaking speed: 40 rpm) for 30 minutes to digest (1-4)-α-D-glucan. The sample was then cooled to room temperature and the pH was adjusted to 7.5 by adding 6N NaOH. Protease (50 mg/l g sample) was added to the sample in 60° C. water bath (shaking speed: 40 rpm) for 30 minutes to remove the protein content. The sample was again cooled to room temperature and the pH was adjusted to 4.5 by adding 6N HCl. Amyloglucosidase (300 μl/1 g sample) was added into the sample in 60° C. water bath (shaking speed: 40 rpm) for 30 minutes to digest the digestible α-D-1,4, 1,6 glucan. To inhibit the enzyme activity, the sample was heated to 100° C. for 30 minutes, and then cooled to room temperature. The sample was centrifuged at 3,500 rpm for 30 minutes. The supernatant was precipitated with 4-volume of alcohol, and the precipitate was collected as the SH-EA sample. The SH and SH-EA samples were subjected to the neutralization test as described above to measure the inhibition of cytopathic effect induced by EV71/TW/4643/1998 on RD cells.

The data summarized in Table 19 indicate that the SH-EA (i.e., the SH extract treated with various digestive enzymes) has a lower $EC_{50}$ than the SH extract. These data suggest that the present SH extract may elicit desirable antiviral activity even after it has been digested. Therefore, it is very likely that the AM extract, upon enteral administration (e.g., oral administration), can retain its antiviral activity in vivo.

TABLE 19

Antiviral activity of AM extract after digestive enzymes treatment

| Samples | $EC_{50}$ (μg/ml) |
|---|---|
| SH | 14.25 ± 0.35 |
| SH-EA | 10.62 ± 0.24 |

It will be understood that the above description of embodiments is given by way of example only and that various modifications may be made by those with ordinary skill in the art. The above specification, examples, and data provide a complete description of the structural and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. *Arthrospira maxima* extract (AM extract), comprising at least 30% (wt %) of total sugar in the AM extract, at least 60% (wt %) of neutral and/or positively charged polysaccharides based on the total sugar in the extract, and at least 30 mol % of rhamnose, wherein the most abundant glycosyl linkage is 3-rhap.

2. The AM extract according to the claim 1, wherein the content of the total sugar in the AM extract is 30-75% (wt %).

3. The AM extract according to the claim 1, wherein the AM extract is derived from a high-molecular-weight fraction obtainable using a filter membrane having a molecular weight cut-off (MWCO) of 100 KD.

4. The AM extract according to the claim 1, wherein the content of neutral and/or positively charged polysaccharides based on the total sugars in the extract is 60-100% (wt %).

5. The AM extract according to claim 1, wherein the AM extract is derived from a high-molecular-weight fraction obtainable using a filter membrane having a molecular weight cut-off (MWCO) of 100 KD, and comprises at least 60% (wt %) of neutral and/or positively charged polysaccharides based on the total sugars in the extract.

6. A nutraceutical composition, comprising a nutraceutically-acceptable excipient and AM extract according to claim 1.

7. A pharmaceutical composition for treating a viral infection caused by Enterovirus virus (EV), respiratory syncytial virus (RSV), Human Herpesvirus (HHV), Ebola virus, porcine epidemic diarrhea virus (PEDV), or porcine reproductive and respiratory syndrome virus (PRRSV), or a disorder caused by the viral infection, wherein the pharmaceutical composition comprises AM extract according to claim 1 and a pharmaceutically acceptable excipient.

* * * * *